US010494618B2

(12) United States Patent
Atares-Real et al.

(10) Patent No.: US 10,494,618 B2
(45) Date of Patent: Dec. 3, 2019

(54) PHYTASE, METHOD FOR OBTAINING THE SAME AND USE THEREOF

(71) Applicant: Fertinagro Nutrientes, S.L., Teruel (ES)

(72) Inventors: Sergio Atares-Real, Teruel (ES); Julia Martin-Perez, Teruel (ES); Joaquin Romero-Lopez, Teruel (ES); Ignasi Salaet-Madorran, Teruel (ES); Ramón Marques-Mascarell, Teruel (ES); Rosa Aligue, Barcelona (ES)

(73) Assignee: Fertinagro Biotech, S.L., Teruel (ES)

( * ) Notice: Subject to any disclaimer, the term of this patent is extended or adjusted under 35 U.S.C. 154(b) by 202 days.

(21) Appl. No.: 15/524,885

(22) PCT Filed: Nov. 5, 2015

(86) PCT No.: PCT/EP2015/075834
§ 371 (c)(1),
(2) Date: May 5, 2017

(87) PCT Pub. No.: WO2016/071458
PCT Pub. Date: May 12, 2016

(65) Prior Publication Data
US 2019/0071654 A1 Mar. 7, 2019

(30) Foreign Application Priority Data
Nov. 6, 2014 (EP) ..................................... 14192111

(51) Int. Cl.
*C12N 9/16* (2006.01)
*A23K 20/189* (2016.01)
(52) U.S. Cl.
CPC .............. *C12N 9/16* (2013.01); *A23K 20/189* (2016.05); *C12Y 301/03008* (2013.01)
(58) Field of Classification Search
CPC . C12Y 301/03008; C12N 9/16; A61K 35/741
See application file for complete search history.

(56) References Cited

FOREIGN PATENT DOCUMENTS

| EP | 2743347 | * | 6/2014 |
|---|---|---|---|
| EP | 2743347 A2 | | 6/2014 |
| JP | 2009535043 A | | 10/2009 |
| JP | 2012527247 A | | 11/2012 |
| RU | 2421519 C2 | | 8/2009 |
| WO | 2007128160 A1 | | 11/2007 |
| WO | 2010/135588 A2 | | 11/2010 |
| WO | WO 2011141613 | * | 11/2011 |

OTHER PUBLICATIONS

Alique et al., "Serratia Odorifera Phytase Gene, SEQ ID 1.", XP002736899, retrieved from EBI accession No. GSN: AZP80408; Database accession No. AZP80408 sequence & Database Geneseq [online], Jan. 5, 2012, 1 page.
Muzny D., et al. "3-phytase; EC=3.1.3.8", Uniprot, XP002674957, sequence, Jan. 1, 2010, 1 page.
Mimi Yang et al. "Enhancement of alkaline phytase production in Pichia Pastoris: Influence of Gene Dosage, Sequence Optimization and Expression Temperature", Protein Expression and Purification, vol. 84, No. 2, Jun. 15, 2012, 8 pages.
Rui Zhang et al., "Two Types of Phytases (Histidine Acid Phytase and β-Propeller Phytase) in *Serratia* sp. TN49 from the Gut of Batocera horsfieldi, (Coleoptera) Larvae", Current Microbiology, Springer-Verlag, NE, vol. 63, No. 5, Aug. 19, 2011, 8 pages.
Extended European Search Report in European Application No. 14192111.4, dated Mar. 26, 2015, 7 pages.
International Search Report and Written Opinion cited in PCT/EP2015/075834, dated Jan. 12, 2016, 15 pages.
International Preliminary Report on Patentability (Chapter I) and Written Opinion dated May 9, 2017, cited in the corresponding International Application No. PCT/EP2015/075834, 8 pages.
UniProtKB D4DZK6 (D4DZK6_SEROD), May 18, 2010, Found on the Internet: www.uniprotorg/uniprot/D4DZK6, 5 pages.
Russian Office Action dated Mar. 7, 2019, in the corresponding application No. 2017118157 including a Search Report, 8 pages.
Russian Office Action dated Jul. 26, 2019 in corresponding application No. 2017118157, 4 pages, and machine translation into English.
Notification of Reasons for Refusal cited in Japanese Application No. 2017-543885, dated Sep. 17, 2019, 11 pages. (including English translation).

* cited by examiner

*Primary Examiner* — Karen Cochrane Carlson
(74) *Attorney, Agent, or Firm* — Rothwell, Figg, Ernst & Manbeck, P.C.

(57) ABSTRACT

The invention generally relates to novel and improved nucleic acid sequences encoding a polypeptide or protein having the enzymatic activity of a phytase and methods for effectively expressing such enzymes in a host cell. In a first aspect, the present invention relates an isolated nucleic acid molecule i) comprising the nucleotide sequence according to SEQ ID NO: 1 encoding a protein with phytase activity or ii) having a sequence identity of at least 83% to a nucleotide sequence according to SEQ ID NO: 1 encoding a protein with phytase activity. The present invention also relates to an expression construct or a vector comprising the above mentioned isolated nucleic acid molecule. The present invention further relates to a method of producing a protein having the enzymatic activity of a phytase comprising the steps of: a) introducing into a host cell a vector comprising: i) elements regulating the expression that are functional in the host cell; and ii) operatively linked thereto a nucleic acid molecule according to the invention; b) cultivating the host cells obtained in step a) under conditions suitable for expression of the protein, and optionally c) recovering the protein produced in step b) from the cell culture. The present invention further relates to proteins obtained by the method according to the invention and the use thereof for the manufacture of additives for animal feed.

20 Claims, 9 Drawing Sheets

Specification includes a Sequence Listing.

Figure 6

**Figure 6A: Wild type *Serratia odorifera* phytase gene sequence (SEQ ID NO: 2)**

```
atgttgctattgcaaaaggactggtcgcgtctgttatttgccgtcacgctgggtatgatttccagc
gtagcccaggctgagccgcgctacgtattggaaaaggtggttgaggtcagccgccacggcgtacgc
cgccgacctcaggcaaccggcaggcgatgcaggcgggaaccggccgagagtggccacaatggctg
acgcgcgacggcgaactcactggccacggttatgccgccgccacgctgaaaggacgctatgaagcc
gactattatcgccgtcagggcctattggccaacggctgtccgagcgcggggcggtgtatgtctgg
gccagtccgctacagcgcacgcgagccaccgcacaggcgttgatggacggcgcatttcccggctgc
ggggtcgccattcatgcggccgccaccgaacaggaccccctgtttcaggcagataaaatgggcctg
gtgccgctcgatgccgaacgggctcgcacggcaataaggcaggcaatgggcggcagcgccgagcag
gtgaaaacgcgctttagcgctgacattcggcgtctgcaagcggcggtctgcctgccgcaacaggct
tgcccggcctttgaacaaccgtgggaaatcactcaggagcacgacggccgcttcagcatcaacggt
ctggggacgttgtccaacatggcggaaagcattcgcctggcctacagcgaaaaccagccgacggcg
caggtcgcctttggccacggtgtcaacgcatcggccgtcgcgccgttgctgcccctgctcaccgcc
cgctatgactttaccaatgacgtgccctatatcgcgcaacgcggtggctcggtgctgttaaaccaa
atcgcgctggcgctggccgccgatcgaacctctgccggggcgccaccggcggcgcgctggttgctg
tttgtcgcgcatgacaccaatatcgcttatctgcgcaccctgcttggctttagctggcaacagggg
ctttacccacgcggcaatattccccggctggcagtctggtattcgaacgctggcgcgatcggcaa
acgggccagcgcttcctgcgtctgtacttccaggcgcaatcgctggatcaaatccgccagttgtca
ccgctgagcacgctgtcgccaccgttaaaaaccgagttcagccgtcctggctgccggcagttgtca
ctgggcgtactctgtccctggactgagtcgatgcaacggatgcgcgcggctatcgacccgacggcg
ctgcctacggtgcagtaccggccataa
```

**Wild type *Serratia odorifera* phytase gene sequence without the nucleotide sequence encoding the N-terminal signal peptide sequence (SEQ ID NO: 8)**

```
gagccgcgctacgtattggaaaaggtggttgaggtcagccgccacggcgtacgcccgccgacctca
ggcaaccggcaggcgatgcaggcgggaaccggccgagagtggccacaatggctgacgcgcgacggc
gaactcactggccacggttatgccgccgccacgctgaaaggacgctatgaagccgactattatcgc
cgtcagggcctattggccaacggctgtccgagcgcggggcggtgtatgtctgggccagtccgcta
cagcgcacgcgagccaccgcacaggcgttgatggacggcgcatttcccggctgcggggtcgccatt
catgcggccgccaccgaacaggaccccctgtttcaggcagataaaatgggcctggtgccgctcgat
gccgaacgggctcgcacggcaataaggcaggcaatgggcggcagcgccgagcaggtgaaaacgcgc
tttagcgctgacattcggcgtctgcaagcggcggtctgcctgccgcaacaggcttgcccggccttt
gaacaaccgtgggaaatcactcaggagcacgacggccgcttcagcatcaacggtctggggacgttg
tccaacatggcggaaagcattcgcctggcctacagcgaaaaccagccgacggcgcaggtcgccttt
ggccacggtgtcaacgcatcggccgtcgcgccgttgctgcccctgctcaccgcccgctatgacttt
accaatgacgtgccctatatcgcgcaacgcggtggctcggtgctgttaaaccaaatcgcgctggcg
ctggccgccgatcgaacctctgccggggcgccaccggcggcgcgctggttgctgtttgtcgcgcat
gacaccaatatcgcttatctgcgcaccctgcttggctttagctggcaacaggggctttacccacgc
ggcaatattccccggctggcagtctggtattcgaacgctggcgcgatcggcaaacgggccagcgc
ttcctgcgtctgtacttccaggcgcaatcgctggatcaaatccgccagttgtcaccgctgagcacg
ctgtcgccaccgttaaaaaccgagttcagccgtcctggctgccggcagttgtcactgggcgtactc
tgtccctggactgagtcgatgcaacggatgcgcgcggctatcgacccgacggcgctgcctacggtg
cagtaccggccataa
```

**Figure 6B: Optimized *Serratia odorifera* phytase nucleotide sequence (optima phytase) (SEQ ID NO: 1)**

```
Gag cct aga tac gtt ttg gaa aag gtg gtt gag gtc tct cga cac ggc
gtt aga cca cca acc tca ggt aac aga cag gct atg caa gcg gga acc
gga agg gag tgg cca caa tgg ctg act cgt gac gga gaa cta act gga
cac ggt tat gca gcc gca aca ctt aaa gga aga tac gaa gcc gat tat
tat aga cgt cag ggc cta ttg gca aac ggt tgt cca tct gct ggg gct
gtt tac gtc tgg gct agt cct cta caa aga aca agg gcc acc gca cag
gct ttg atg gac ggt gca ttt ccc gga tgc ggg gtc gcc att cat gct
gca gcc act gaa caa gat ccc ttg ttt caa gca gat aag atg ggt ctt
gtt cca ctc gat gcc gaa agg gct aga act gca ata agg cag gca atg
ggt ggc tca gcc gag caa gtg aag aca cgt ttt agt gct gac att agg
cgt ctg caa gct gct gtt tgt ttg cct caa cag gct tgt cct gcc ttt
gaa caa cct tgg gaa att act caa gag cat gac ggt aga ttc agc atc
aat ggt cta gga aca ttg tcc aat atg gct gaa tct att aga ctt gcc
tac tct gaa aac cag cca acg gct caa gtc gca ttt gga cac ggt gtc
aac gca tcc gcc gtc gct cct ttg tta cca ctg cta acc gcc aga tat
gac ttt acc aat gat gtg ccc tat atc gct caa aga ggt ggc tcc gtt
ctg tta aac caa att gct ttg gct ctt gcc gca gat agg act tct gcc
ggg gcg cca cct gct gct cgt tgg ttg tta ttt gtc gct cat gac acc
aat atc gct tat tta aga act ctg ctt ggt ttt tct tgg caa cag gga
ctt tac cca aga ggt aat att ccc cct gct gga agt ttg gtt ttc gaa
aga tgg cgt gat aga caa aca ggt caa agg ttc tta cgt ctg tac ttc
cag gct caa tcg ttg gat caa atc aga cag ttg tca cca ctt tct aca
tta tcc cca cct tta aaa acc gag ttc tct cgt cct ggt tgc agg cag
ttg tca ctt ggc gtt ctc tgt ccc tgg act gag tcc atg caa aga atg
aga gct gct atc gac cca act gcg ttg cct aca gtg cag tac aga cca
taa
```

Figure 6C: Amino acid sequence of the optimized phytase protein (SEQ ID NO: 3)

EPRYVLEKVVEVSRHGVRPPTSGNRQAMQAGTGREWPQWLTRDGELTGHGYAAATLK
GRYEADYYRRQGLLANGCPSAGAVYVWASPLQRTRATAQALMDGAFPGCGVAIHAAA
TEQDPLFQADKMGLVPLDAERARTAIRQAMGGSAEQVKTRFSADIRRLQAAVCLPQQ
ACPAFEQPWEITQEHDGRFSINGLGTLSNMAESIRLAYSENQPTAQVAFGHGVNASA
VAPLLPLLTARYDFTNDVPYIAQRGGSVLLNQIALALAADRTSAGAPPAARWLLFVA
HDTNIAYLRTLLGFSWQQGLYPRGNIPPAGSLVFERWRDRQTGQRFLRLYFQAQSLD
QIRQLSPLSTLSPPLKTEFSRPGCRQLSLGVLCPWTESMQRMRAAIDPTALPTVQYR
P

Figure 6D: Amino acid sequence of the Amino acid sequence comparison between the translated sequence of Fig 6A and the translated sequence of Fig 6B.

```
>ref|ZP_06638020.1|  3-phytase [Serratia odorifera DSM 4582]
 gb|EFE96977.1|  3-phytase [Serratia odorifera DSM 4582]
Length=426

Score =   792 bits (2046),  Expect = 0.0, Method: Compositional matrix adjust.
 Identities = 400/400 (100%), Positives = 400/400 (100%), Gaps = 0/400 (0%)
 Frame = +1

Query  1     EPRYVLEKVVEVSRHGVRPPTSGNRQAMQAGTGREWPQWLTRDGELTGHGYAAATLKGRY  180
             EPRYVLEKVVEVSRHGVRPPTSGNRQAMQAGTGREWPQWLTRDGELTGHGYAAATLKGRY
Sbjct  27    EPRYVLEKVVEVSRHGVRPPTSGNRQAMQAGTGREWPQWLTRDGELTGHGYAAATLKGRY  86

Query  181   EADYYRRQGLLANGCPSAGAVYVWASPLQRTRATAQALMDGAFPGCGVAIHAAATEQDPL  360
             EADYYRRQGLLANGCPSAGAVYVWASPLQRTRATAQALMDGAFPGCGVAIHAAATEQDPL
Sbjct  87    EADYYRRQGLLANGCPSAGAVYVWASPLQRTRATAQALMDGAFPGCGVAIHAAATEQDPL  146

Query  361   FQADKMGLVPLDAERARTAIRQAMGGSAEQVKTRFSADIRRLQAAVCLPQQACPAFEQPW  540
             FQADKMGLVPLDAERARTAIRQAMGGSAEQVKTRFSADIRRLQAAVCLPQQACPAFEQPW
Sbjct  147   FQADKMGLVPLDAERARTAIRQAMGGSAEQVKTRFSADIRRLQAAVCLPQQACPAFEQPW  206

Query  541   EITQEHDGRFSINGLGTLSNMAESIRLAYSENQPTAQVAFGHGVNASAVAPLLPLLTARY  720
             EITQEHDGRFSINGLGTLSNMAESIRLAYSENQPTAQVAFGHGVNASAVAPLLPLLTARY
Sbjct  207   EITQEHDGRFSINGLGTLSNMAESIRLAYSENQPTAQVAFGHGVNASAVAPLLPLLTARY  266

Query  721   DFTNDVPYIAQRGGSVLLNQIALALAADRTSAGAPPAARWLLFVAHDTNIAYLRTLLGFS  900
             DFTNDVPYIAQRGGSVLLNQIALALAADRTSAGAPPAARWLLFVAHDTNIAYLRTLLGFS
Sbjct  267   DFTNDVPYIAQRGGSVLLNQIALALAADRTSAGAPPAARWLLFVAHDTNIAYLRTLLGFS  326

Query  901   WQQGLYPRGNIPPAGSLVFERWRDRQTGQRFLRLYFQAQSLDQIRQlsplstlsppKTE   1080
             WQQGLYPRGNIPPAGSLVFERWRDRQTGQRFLRLYFQAQSLDQIRQLSPLSTLSPPLKTE
Sbjct  327   WQQGLYPRGNIPPAGSLVFERWRDRQTGQRFLRLYFQAQSLDQIRQLSPLSTLSPPLKTE  386

Query  1081  FSRPGCRQLSLGVLCPWTESMQRMRAAIDPTALPTVQYRP  1200
             FSRPGCRQLSLGVLCPWTESMQRMRAAIDPTALPTVQYRP
Sbjct  387   FSRPGCRQLSLGVLCPWTESMQRMRAAIDPTALPTVQYRP  426
```

Figure 6E: nucleotide comparison of gene sequence of Fig 6A (SEQ ID NO: 8, upper sequence) and gene sequence of Fig 6B (SEQ ID NO: 1, lower sequence).

```
Length=1203

Score =  1218 bits (1350),  Expect = 0.0
 Identities = 992/1203 (82%), Gaps = 0/1203 (0%)
 Strand=Plus/Plus Query  1     GAGCCGCGCTACGTATTGGAAAAGGTGGTTGAGGTCAGCCGCCACGGCGTACGCCCGCCG  60
             |||||  |  ||||| |||||||||||||||||||  || ||||||| |  || || ||
Sbjct  1     GAGCCTAGATACGTTTTGGAAAAGGTGGTTGAGGTCTCTCGACACGGCGTTAGACCACCA  60

Query  61    ACCTCAGGCAACCGGCAGGCGATGCAGGCGGGAACCGGCCGAGAGTGGCCACAATGGCTG  120
             ||||||||  ||| | |||||  |||||  ||||||||  |  ||||||||||||||||
Sbjct  61    ACCTCAGGTAACAGACAGGCTATGCAAGCGGGAACCGGAAGGGAGTGGCCACAATGGCTG  120

Query  121   ACGCGCGACGGCGAACTCACTGGCCACGGTTATGCCGCCGCCACGCTGAAAGGACGCTAT  180
             || || |||||  |||| ||||| ||||||||||| ||||| ||| || ||||| | ||
Sbjct  121   ACTCGTGACGGAGAACTAACTGGACACGGTTATGCAGCCGCAACACTTAAAGGAAGATAC  180

Query  181   GAAGCCGACTATTATCGCCGTCAGGGCCTATTGGCCAACGGCTGTCCGAGCGCGGGGGCG  240
             ||||||||  ||||||  ||| || |||||||||||||  |||  ||  |||    |||
Sbjct  181   GAAGCCGATTATTATAGACGTCAGGGCCTATTGGCAAACGGTTGTCCATCTGCTGGGGCT  240

Query  241   GTGTATGTCTGGGCCAGTCCGCTACAGCGCACGCGAGCCACCGCACAGGCGTTGATGGAC  300
             ||  |  |||||||| ||  ||  |||   |||   ||||||||||||||| ||||| |
Sbjct  241   GTTTACGTCTGGGCTAGTCCTCTACAAAGAACAAGGGCCACCGCACAGGCTTTGATGGAC  300

Query  301   GGCGCATTTCCCGGCTGCGGGGTCGCCATTCATGCGGCCGCCACCGAACAGGACCCCCTG  360
             ||  |||||||||| || ||||||||||||||||| || || || ||||| ||  ||  
Sbjct  301   GGTGCATTTCCCGGATGCGGGGTCGCCATTCATGCTGCAGCCACTGAACAAGATCCCTTG  360

Query  361   TTTCAGGCAGATAAAATGGGCCTGGTGCCGCTCGATGCCGAACGGGCTCGCACGGCAATA  420
             ||||| ||||||||| |||| | ||| || |||||||||||  ||||| || | ||||| 
Sbjct  361   TTTCAAGCAGATAAGATGGGTCTTGTTCCACTCGATGCCGAAAGGGCTAGAACTGCAATA  420

Query  421   AGGCAGGCAATGGGCGGCAGCGCCGAGCAGGTGAAAACGCGCTTTAGCGCTGACATTCGG  480
             ||||||||||||||  | |||||||||| |||| ||| ||||||| | |||||||| ||
Sbjct  421   AGGCAGGCAATGGGTGGCTCAGCCGAGCAAGTGAAGACACGTTTTAGTGCTGACATTAGG  480

Query  481   CGTCTGCAAGCGGCGGTCTGCCTGCCGCAACAGGCTTGCCCGGCCTTTGAACAACCGTGG  540
             ||||||||||| ||||  |  |  ||||||||||||| |  ||| |||||||||| |||
Sbjct  481   CGTCTGCAAGCTGCTGTTTGTTTGCCTCAACAGGCTTGTCCTGCCTTTGAACAACCTTGG  540

Query  541   GAAATCACTCAGGAGCACGACGGCCGCTTCAGCATCAACGGTCTGGGGACGTTGTCCAAC  600
             ||||| ||| ||||| || || |   ||| ||||||| ||| | || || |||||| | 
Sbjct  541   GAAATTACTCAAGAGCATGACGGTAGATTCAGCATCAATGGTCTAGGAACATTGTCCAAT  600

Query  601   ATGGCGGAAAGCATTCGCCTGGCCTACAGCGAAAACCAGCCGACGGCGCAGGTCGCCTTT  660
             |||||  ||| ||| | || |   || ||| |||||||||| ||||| ||||| ||||| 
Sbjct  601   ATGGCTGAATCTATTAGACTTGCCTACTCTGAAAACCAGCCAACGGCTCAAGTCGCATTT  660

Query  661   GGCCACGGTGTCAACGCATCGGCCGTCGCGCCGTTGCTGCCCCTGCTCACCGCCCGCTAT  720
             ||  ||||||||||||||| ||||||||  ||||  |||||| |||| ||||||| |||
Sbjct  661   GGACACGGTGTCAACGCATCCGCCGTCGCTCCTTTGTTACCACTGCTAACCGCCAGATAT  720

Query  721   GACTTTACCAATGACGTGCCCTATATCGCGCAACGCGGTGGCTCGGTGCTGTTAAACCAA  780
             |||||||||||||| |||||||||||||| ||| | |||||||| ||| |||||||||
Sbjct  721   GACTTTACCAATGATGTGCCCTATATCGCTCAAAGAGGTGGCTCCGTTCTGTTAAACCAA  780

Query  781   ATCGCGCTGGCGCTGGCCGCCGATCGAACCTCTGCCGGGGCGCCACCGGCGGCGCGCTGG  840
             || ||   |||||| || ||| | |  |  || |||||||||||||| || ||| ||||
Sbjct  781   ATTGCTTTGGCTCTTGCCGCAGATAGGACTTCTGCCGGGGCGCCACCTGCTGCTCGTTGG  840

Query  841   TTGCTGTTTGTCGCGCATGACACCAATATCGCTTATCTGCGCACCCTGCTTGGCTTTAGC  900
             |||  | |||||||||||||||||||||||||||||    |   ||||||||| |||| 
Sbjct  841   TTGTTATTTGTCGCTCATGACACCAATATCGCTTATTTAAGAACTCTGCTTGGTTTTTCT  900
```

Fig. 6E Continued

```
Query  901   TGGCAACAGGGGCTTTACCCACGCGGCAATATTCCCCCGGCTGGCAGTCTGGTATTCGAA  960
             |||||||||||| |||||||||| |  || ||||||||||| ||||| ||| |||| |||||
Sbjct  901   TGGCAACAGGGACTTTACCCAAGAGGTAATATTCCCCCTGCTGGAAGTTTGGTTTTCGAA  960

Query  961   CGCTGGCGCGATCGGCAAACGGGCCAGCGCTTCCTGCGTCTGTACTTCCAGGCGCAATCG  1020
             |  ||||| ||| | ||||| || ||  | | ||| | |||||||||||||||| ||||||
Sbjct  961   AGATGGCGTGATAGACAAACAGGTCAAAGGTTCTTACGTCTGTACTTCCAGGCTCAATCG  1020

Query  1021  CTGGATCAAATCCGCCAGTTGTCACCGCTGAGCACGCTGTCGCCACCGTTAAAAACCGAG  1080
             |||||||||| | |||||||||||||  ||   || | || ||||| ||||||||||||||
Sbjct  1021  TTGGATCAAATCAGACAGTTGTCACCACTTTCTACATTATCCCCACCTTTAAAAACCGAG  1080

Query  1081  TTCAGCCGTCCTGGCTGCCGGCAGTTGTCACTGGGCGTACTCTGTCCCTGGACTGAGTCG  1140
             |||   |||||||| ||||||||||||||||| ||||| |||||||||||||||||||||
Sbjct  1081  TTCTCTCGTCCTGGTTGCAGGCAGTTGTCACTTGGCGTTCTCTGTCCCTGGACTGAGTCC  1140

Query  1141  ATGCAACGGATGCGCGCGGCTATCGACCCGACGGCGCTGCCTACGGTGCAGTACCGGCCA  1200
             |||||| | |||  |  || ||||||||||| || ||| |||||| ||||||||| | |||
Sbjct  1141  ATGCAAAGAATGAGAGCTGCTATCGACCCAACTGCGTTGCCTACAGTGCAGTACAGACCA  1200

Query  1201  TAA  1203
             |||
Sbjct  1201  TAA  1203
```

Example 5

|  | Wild type phytase | | | | | | | |
|---|---|---|---|---|---|---|---|---|
| Time after induction (hours) | 0 | 19 | 31 | 43 | 55 | 67 | 79 | 91 |
| Units/ml | 0 | 0 | 0 | 0 | 0 | 0 | 0 | 0 |
| Units/L | 1 | 1 | 1 | 1 | 21 | 57 | 68 | 143 |

|  | Optima phytase | | | | | | | |
|---|---|---|---|---|---|---|---|---|
| Time after induction (hours) | 0 | 19 | 31 | 43 | 55 | 67 | 79 | 91 |
| Units/ml | 0 | 2 | 6 | 15 | 15 | 20 | 28 | 30 |
| Units/L | 1 | 2163 | 6430 | 14914 | 15059 | 19797 | 27846 | 29973 |

PHYTASE, METHOD FOR OBTAINING THE SAME AND USE THEREOF

CROSS REFERENCE TO RELATED APPLICATION

This application is a 35 U.S.C. 371 National Phase Entry Application from PCT/EP2015/075834, filed Nov. 5, 2015, which claims the benefit of European Patent Application No. 14192111.4, filed on Nov. 6, 2014, the disclosures of which are incorporated by reference in their entirety.

The present application includes a Sequence Listing filed in electronic format. The Sequence Listing is entitled "3934-132June.2019_ST25.txt" created on June 5, 2019, and is 10,000 bytes in size. The information in the electronic format of the Sequence Listing is part of the present application and is incorporated herein by reference in its entirety.

FIELD OF THE INVENTION

The invention generally relates to novel and improved nucleic acid sequences encoding a polypeptide or protein having the enzymatic activity of a phytase and methods for effectively expressing such enzymes in a host cell.

In a first aspect, the present invention relates an isolated nucleic acid molecule i) comprising the nucleotide sequence according to SEQ ID NO: 1 encoding a protein with phytase activity or ii) having a sequence identity of at least 78% to a nucleotide sequence according to SEQ ID NO: 1 encoding a protein with phytase activity.

The present invention also relates to an expression construct or a vector comprising the above mentioned isolated nucleic acid molecule. The present invention further relates to a method of producing a protein having the enzymatic activity of a phytase comprising the steps of:
a) introducing into a host cell a vector comprising:
i) elements regulating the expression that are functional in the host cell; and
ii) operatively linked thereto a nucleic acid molecule as defined herein;
b) cultivating the host cells obtained in step a) under conditions suitable for expression of the protein, and optionally
c) recovering the protein produced in step b) from the cell culture.

The present invention further relates to proteins obtained by the method according to the invention and the use thereof for the manufacture of additives for animal feed.

BACKGROUND OF THE INVENTION

The invention generally relates to novel nucleic acid molecules encoding a polypeptide or protein having the enzymatic activity of a phytase and to a method for effectively producing such a protein with phytase activity in a host cell. The invention also relates a polypeptide or protein obtained by the method according to the present invention and the use thereof as an active ingredient in the fabrication of additives for animal feed and/or for the release of phosphate of the organic material coming from the soil.

Elemental or pure phosphorus (P) is quite uncommon in nature, which is usually found as part of molecules which include the phosphate group ($PO_4^{3-}$) joined to an organic group based on carbon of animals and plant tissues.

However, phosphorus (P) is an important nutrient for plants and animals. P is an important plant macronutrient, making up about 0.2% of a plant's dry weight. It is a component of key molecules such as nucleic acids, phospholipids, and ATP, and, consequently, plants cannot grow without a reliable supply of this nutrient. Inorganic phosphorus is the only source of phosphorous that can be absorbed and taken up by plants. Due to the only low availability of inorganic phosphorus in the soil, the farmers are forced to make available the macronutrient P.

Also animals require phosphorus as a nutrient, which can be generally provided either in the form of inorganic phosphorus, for instance, in a diet or by the degradation of the organic phosphorus various ingredients making up the diet.

The phytic acid or phytate is the major storage form of phosphorus in plants such as cereals, pulses, oilseeds, with values ranging from 1 to 5% by weight. "Phytic acid", also referred to as inositol hexakisphosphate (IP6), or the salt thereof "phytate", is a saturated cyclic acid. Moreover, phytic acid typically chelates and thus makes unabsorbable certain important minor minerals such as zinc and iron, and to a lesser extent, also macro minerals such as calcium and magnesium. Phytin refers specifically to the calcium or magnesium salt form of phytic acid. Catabolites of phytic acid are called lower inositol polyphosphates. Examples are inositol penta-(IP5), tetra-(IP4), and triphosphate (IP3). More than two-thirds of the phosphorus contained in the cereals and legumes are present in phytate form.

Phytate is not digestible to humans or nonruminant animals (monogastric animals), so that is is not an appropriate source of either inositol or phosphate, if eaten directly. In particular, the phosphorus and inositol present in the phytate form cannot be made bioavailable to non-ruminant animals, because they lack the digestive enzyme phytase that is required to remove phosphate from the inositol in the phytate molecule. The phosphorous present in the phytate form constitutes about between 20 and 40% of the phosphorus of vegetal origin ingested by monogastric animals.

Since phytate cannot be adsorbed by non-ruminant animals the unabsorbed phytate usually passes through the gastrointestinal tract, elevating the amount of phosphorus in the manure. Excess phosphorus excretion can lead to environmental and ecological problems, such as eutrophication. The contamination of the soil with phosphorus poses a severe problem in agriculture, especially in areas of intensive agricultural with monogastric animals.

Moreover, although some of the microorganisms in intestinal flora in the small intestine are capable of hydrolyzing phytic acid, the phosphorus is only absorbed in small amounts. On the other hand, an excess of phytate has the effect of an anti-nutritional factor since phytate is capable of chelating essential metal ions such as calcium, copper or zinc, which are necessary for animal nutrition, thereby decreasing its nutritional value.

To avoid the above mentioned drawbacks, animal food was commonly enriched with inorganic phosphorus, which in turn increased the costs of livestock production. One further approach which came up recently to alleviate these drawbacks is the direct addition of phytase, which catalyzes the hydrolysis of phytate to release and make available and accessible organic phosphorus to animal food.

The use of microbial phytase is currently approved for use in animal feed, with the purpose to increase the availability of phosphorus from phytic acid. For instance, 6-phytase produced by *Aspergillus oryzae* (DSM 14223) was authorized for fattening chicken, laying hens, fattening turkeys, fattening pigs and female pigs by Regulation (EC) No 255/2005 of the European Commission. These phytases are extremely weak and unstable, expressing the maximum activity of pH between 5.0 and 7.5, so that activity is substantially reduced and limited due to the low pH values in the stomach (pH 2-3). Phytase enzyme are also known to be strongly inhibited by excess of substrate (phytate) and product (inorganic phosphorus), and high temperatures (Power and Khon, 1993).

The synthetic phytases are phosphomonoesterases capable of hydrolyzing phytic acid to inorganic orthophosphate with low proportions of phosphoric esters, with pentaphosphate to monophosphate being intermediate products, and free myoinositol (Nayini and Markakis, 1986; Lasztity and Lasztity, 1988; Harland and Morris, 1995). The IUPAC-IUB (1976) has recognized the 3-phytase (EC 3.1.3.8), isolated in animals and microorganisms (Reddy and col., 1982; Lasztity and Lasztity, 1988).

Exogenous phytases have been found in microorganisms such as fungi and yeasts (e.g. *Saccharomyces cerevisae* and *Aspergillus* sp), and bacteria (*Bacillus subtilis, Pseudomonas*). The phytase which is obtained from *Aspergillus* sp follows certain order of hydrolyzing the phytate molecule, i.e. after having released the phosphate group from position 3, continue in the following order, 4, 5, 6 and 2 (Venekamp et al., 1995). These enzymes show activity at different pH 2.5 and H5.5. The activity at pH 2.5 is about 40% less effective than at pH 5.5, which is important since absorption of phosphorus occurs to a greater extent at the small intestine having a pH 5.5. (Power and Khon, 1993).

The phytase produced by *Aspergillus ficuumm*, is a purified glycoprotein, with an enzymatic activity that changes with temperature and pH. The optimal temperature of the enzyme is between 60 to 70° C. However, during 10 minutes at 68° C. a loss of activity to 60% was a observed (Nasi, 1990). The thermo-stable *Aspergillus niger* enzymes are resistant against the pelleting process and its activity is reported to be at least 5000 FTU/g. (Nasi, 1990).

WO 2011/141613 A2 describes a novel isolated gene of *Serratia odorifera*, which encodes a protein or polypeptide having phytase activity, a process for obtaining the same in a host yeast cell like, such as *Pichia pastoris*, and the use of the enzyme as an active ingredient in the fabrication of additives for animal feed. WO 2011/141613 reports on a phytase, which was not sensitive to the pH difference between the stomach (pH 3.5) and the intestinal tract (pH 7.0) and which maintained its activity over a broad pH range. The phytase described in WO 2011/1416 was reported to have improved thermo-stability.

However, the modest expression level of this *Serratia* phytase wild type protein still represents a bottleneck with regard to large scale protein production. There is still a strong need to identify the factors and conditions leading to an improved and effective expression of the phytase protein in a host cell. The state of the art still lacks means and methods capable of efficiently producing more protein with phytase activity per volume and over the time. Hence, there is still a strong need to improve the conditions of industrial scale production in order to provide a cost efficient and reliable method.

SUMMARY OF THE INVENTION

The above object is solved by the methods and means according to the present invention as described and claimed herein. The present invention addresses these needs and provides a novel isolated nucleic acid molecule of *Serratia odorifera* encoding a protein or polypeptide with phytase activity. The present invention further provides methods for effectively expressing and subsequent purifying the isolated genes according to the invention in a host cell.

In a first aspect the present invention relates to an isolated nucleic acid molecule
i) comprising the nucleotide sequence according to SEQ ID NO: 1 encoding a protein with phytase activity or
ii) having a sequence identity of at least 83% to a nucleotide sequence according to SEQ ID NO: 1 encoding a protein with phytase activity.

In a further preferred embodiment the isolated nucleic acid molecule has sequence identity of at least 90% to a nucleotide sequence according to SEQ ID NO: 1 encoding a a protein with phytase activity.

In yet another preferred embodiment the nucleic acid molecule does not comprise a nucleotide sequence encoding for an N-terminal signal peptide.

In a further preferred embodiment the isolated nucleic acid molecule further comprising codon-optimizes mutations with respect to a host cell organism.

In a further preferred embodiment the host cell organism is *Pichias Pastoris*.

In yet another preferred embodiment of the present invention the nucleic acid molecule differs from the corresponding wild type nucleotide coding sequence by the presence of at least 50 codon optimizing mutations.

In a further preferred embodiment at least 50%, of the codons of the corresponding wild type nucleic acid sequence are modified to the codons most favored by the host cell organism.

In one preferred embodiment all codons in the isolated nucleic acid molecule are modified to the codons most favored by the host cell organism.

In further preferred embodiments the isolated nucleic acid molecule according encodes the amino acid sequence of the protein with phytase activity according to SEQ ID NO: 3.

In a second aspect the present invention relates an expression construct comprising the above mentioned isolated nucleic acid molecule operatively linked to elements regulating the expression of the nucleic acid sequence.

In a preferred embodiment said expression construct the elements regulating the expression comprise a promoter functional in a host cell and optionally a termination sequence.

According to a further preferred embodiment said host cell is a fungal cell.

In yet a further preferred embodiment the fungal cell is *Pichia Pastoris*.

In a third aspect, the invention relates to vector comprising said nucleic acid molecule or the expression construct.

In a fourth aspect the present invention relates to a method of producing a protein having the enzymatic activity of a phytase comprising the steps of:
a) introducing into a host cell a vector comprising:
i) elements regulating the expression that are functional in the host cell; and
ii) operatively linked thereto a nucleic acid molecule encoding a protein with phytase activity as defined herein;
b) cultivating the host cells obtained in step a) under conditions suitable for expression of the protein, and optionally
c) recovering the protein produced in step b) from the cell culture.

In a further embodiment the elements regulating the expression comprise a promoter functional in a host cell and optionally a termination sequence.

In yet another embodiment of the present invention the host cell is yeast cell.

In a further specific embodiment the yeast cell is *Pichia Pastoris*.

In further preferred embodiments of the present the protein expression is carried out using a methanol expression system.

In yet another preferred embodiments the protein recovered in step d) has a phytase activity of at least 1000 Units/L.

In a further preferred embodiment said step of recovering comprises i) separating the secreted protein from the medium and/or i) separating the protein from the host cell.

In a fifth aspect the present invention relates to protein obtained by the method according to the invention.

In a further aspect, the present invention relates to the use of the protein according to the present invention or produced by the method described herein for the manufacture of additives for animal feed.

In yet another aspect, the present invention relates to additives for animal feed comprising the protein described herein or comprising the protein produced by the method described herein.

BRIEF DESCRIPTION OF THE DRAWINGS

The following drawings are illustrative of the embodiments of the invention and are not meant to limit the scope of the invention as encompassed by the claims.

FIG. 6A: Nucleotide sequence of the original *Serratia odorifera* phytase sequence (SEQ ID NO: 2) wild type and the *Serratia odorifera* nucleotide sequence without the nucleotide sequence encoding the N-terminal signal peptide sequence (SEQ ID NO: 8). The nucleotide sequence encoding the N-terminal signal peptide sequence (SEQ ID NO:4) is highlighted in grey.

FIG. 6B: Nucleotide sequence of the optimized/improved *Serratia odorifera* phytase (AppAs-r optima/optima phytase) (SEQ ID NO: 1)

FIG. 6C: Amino acid sequence *Serratia odorifera* AppAs-r optima phytase protein (SEQ ID NO: 3)

FIG. 6D: Amino acid sequence comparison between translated sequence of FIG. 6A (upper sequence) and translated sequence of FIG. 6B (lower sequence). Each aligned sequence is the same as SEQ ID NO: 3.

FIG. 6E: Nucleotide comparison of gene sequence of FIG. 6A (upper sequence) and gene sequence of FIG. 6B (lower sequence).

DETAILED DESCRIPTION OF THE EMBODIMENTS

Figure 1:
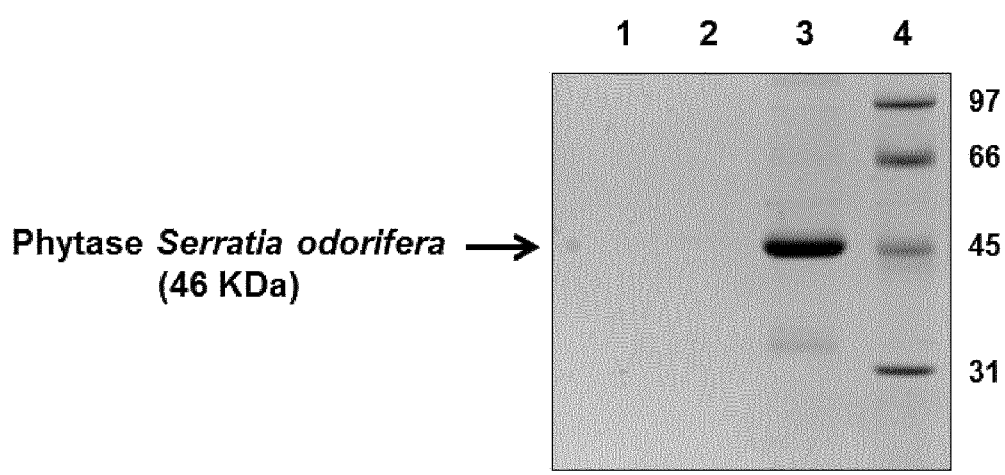
FIG. 1: Determination of the molecular weight of phytase AppAs-r optima protein by denaturing acrylamide gel (SDS-PAGE): Cultivation medium without methanol induction (Lane 1); expression of phytase AppAs-r in cultivation medium with methanol (Lane 2); expression of phytase AppAs-r optima in cultivation medium with methanol (Lane 3); MW marker (Lane 4)

The invention generally relates to novel and improved nucleic acid sequences encoding a polypeptide or protein having the enzymatic activity of a phytase and methods for effectively expressing such enzymes in a host cell.

Although the present invention will be described with respect to particular embodiments, this description is not to be construed in a limiting sense.

Before describing in detail exemplary embodiments of the present invention, definitions important for understanding the present invention are given.

As used in this specification and in the appended claims, the singular forms of "a" and "an" also include the respective plurals unless the context clearly dictates otherwise.

In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%.

It is to be understood that the term "comprising" is not limiting. For the purposes of the present invention the term "consisting of" is considered to be a preferred embodiment of the term "comprising of". If hereinafter a group is defined to comprise at least a certain number of embodiments, this is meant to also encompass a group, which preferably consists of these embodiments only.

Furthermore, the terms "first", "second", "third" or "(a)", "(b)", "(c)", "(d)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

In case the terms "first", "second", "third" or "(a)", "(b)", "(c)", "(d)" "i", "ii" etc. relate to steps of a method or use or assay there is no time or time interval coherence between the steps, i.e. the steps may be carried out simultaneously or there may be time intervals of seconds, minutes, hours, days, weeks, months or even years between such steps, unless otherwise indicated in the application as set forth herein above or below.

It is to be understood that this invention is not limited to the particular methodology, protocols, reagents etc. described herein, as these may vary. It is also to be understood that the terminology used herein is for the purpose of describing particular embodiments only, and is not intended to limit the scope of the present invention that will be limited only by the appended claims. Unless defined otherwise, all technical and scientific terms used herein have the same meanings as commonly understood by one of ordinary skill in the art.

The above object is solved by the methods and means according to the present invention as described and claimed herein. The present invention addresses these needs and provides means and methods for obtaining an isolated gene of *Serratia odorifera* encoding a protein or polypeptide with phytase activity. The present invention further provides methods for effectively expressing and subsequent purifying the isolated genes according to the invention in a host cell.

As used herein the term "gene", refers to a defined region that is located within a genome and that may comprise regulatory, nucleic acid sequences responsible for the control of expression, i.e., transcription and translation of the coding portion. A gene may also comprise other 5' and 3' untranslated sequences and termination sequences. Further elements that may be present are, for example, introns.

An "isolated nucleic acid molecule" encoding the protein with phytase activity according to the present invention refers to a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature.

Isolated nucleic acid molecules are therefore distinguishable from other specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

As used herein, the term "mutation" means any change in a polypeptide or nucleic acid molecule relative to a wild-type polypeptide or nucleic acid molecule from which the 'mutant' is derived and may, for example, comprise single or multiple amino acid or nucleotide changes, or both nucleotide and amino acid changes, including point mutations, null mutations, frame-shift mutations, and may comprise deletions, or insertions, or substitutions of one or more nucleic acids or amino acids, which may comprise naturally or non-naturally occurring nucleotides or amino acids or analogues thereof.

A "nucleic acid" or "nucleic acid molecule", as used to herein, generally refers to deoxyribonucleotides or ribonucleotides and polymers thereof in either single-, double-stranded or triplexed form. The term may encompass nucleic acids containing known analogues of natural nucleotides having similar binding properties as the reference nucleic acid. A particular nucleic acid sequence may also implicitly encompass conservatively modified variants thereof (e.g. degenerate codon substitutions) and complementary sequences. The terms "nucleic acid", "nucleic acid sequence" or "polynucleotide" may also be used interchangeably with gene, cDNA, and mRNA encoded by a gene.

The terms "nucleic acid(s) of the invention" or "nucleic acid molecule(s) of the invention" used herein designate a sequence of nucleotides that may be used per se or in the compositions or methods described herein. The terms refer to the entire coding sequence of a protein or polypeptide from *Serratia odorifera* with phytase activity according to SEQ ID NO: 2 mentioned herein. Furthermore, the terms also designate nucleic acids encoding functional protein fragments, vectors comprising the coding sequences or functional fragments of the above proteins as well as derivatives of the nucleic acids referred to herein, which have modifications, i.e. deletions, additions, inversions, etc. of one or more, e.g. 1 to 50, 1 to 40, 1 to 30, 1 to 20, 1 to 10, 1 to 5, 1 to 3, 2, or 1 nucleotide(s), which nevertheless encode polypeptides substantially having the phytase activity as described for the *Serratia odorifera* phytase according to SEQ ID NO: 2. Functional derivatives of the nucleic acids of the invention encode phytase polypeptides that have at least 10%, 20%, 30%, 40%, 50%, 60%, 70%, 80%, 90% or more phytase activity when compared with the wild-type polypeptide.

Moreover, as indicated above, the terms "nucleic acid(s) of the invention" or "nucleic acid molecule(s) of the invention" designate also vectors comprising the nucleic acids described herein. These vectors may contain regulatory sequences allowing for the efficient transcription and translation of the herein described nucleic acids.

The terms "polypeptide", "peptide" and "protein" may also include polymers including modifications such as, but not limited to, glycosylation, lipid attachment, sulfation, gamma-carboxylation of glutamic acid residues, hydroxylation and ADP-ribosylation.

The term "isolated polypeptide" as used herein describes the various polypeptides disclosed herein, means polypeptide that has been identified and separated and/or recovered from a component of its natural environment. Ordinarily, however, isolated polypeptide will be prepared by at least one purification step.

In a first aspect the present invention relates to an isolated nucleic acid molecule
i) comprising the nucleotide sequence according to SEQ NO: 1 encoding a protein with phytase activity or
ii) having a sequence identity of at least 78% to a nucleotide sequence according to SEQ ID NO: 1 encoding a protein with phytase activity.

The invention provides isolated, synthetic or recombinant nucleic acid molecule comprising (a) a nucleic acid (polynucleotide) encoding at least one polypeptide having phytase activity, wherein the nucleic acid comprises a sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more or complete (100%) sequence identity to the nucleic acid (polynucleotide) sequence of SEQ ID NO:1. In a further preferred embodiment the isolated nucleic acid molecule has sequence identity of at least 90% to a nucleotide sequence encoding a phytase according to SEQ ID NO: 1.

SEQ ID NO: 1 refers to nucleotide sequence of the nucleic acid molecule encoding a protein or polypeptide from *Serratia odorifera* with phytase activity. The nucleotide sequence of this improved or optimized phytase nucleotide sequence is herein referred to as "AppAs-r optima" or "optima phytase" (SEQ ID NO: 1) and depicted in FIG. 6B:

```
                                            SEQ ID NO: 1
gagcctagatacgttttggaaaaggtggttgaggtctctcgacacggc gttagaccaccaacctcaggtaacagacaggctatgcaagcgggaacc ggaagggagtggccacaatggctgactcgtgacggagaactaactgga cacggttatgcagccgcaacacttaaaggaagatacgaagccgattat tatagacgtcagggcctattggcaaacggttgtccatctgctggggct gtttacgtctgggctagtcctctacaaagaacaagggccaccgcacag gctttgatggacggtgcatttcccggatgcggggtcgccattcatgct gcagccactgaacaagatcccttgtttcaagcagataagatgggtctt gttccactcgatgccgaaagggctagaactgcaataaggcaggcaatg ggtggctcagccgagcaagtgaagacacgttttagtgctgacattagg cgtctgcaagctgctgtttgtttgcctcaacaggcttgtcctgcctttt
```

-continued
gaacaaccttgggaaattactcaagagcatgacggtagattcagcatc aatggtctaggaacattgtccaatatggctgaatctattagacttgcc tactctgaaaaccagccaacggctcaagtcgcatttggacacggtgtc aacgcatccgccgtcgctcctttgttaccactgctaaccgccagatat gactttaccaatgatgtgccctatatcgctcaaagaggtggctccgtt ctgttaaaccaaattgctttggctcttgccgcagataggacttctgcc ggggcgccacctgctgctcgttggttgttatttgtcgctcatgacacc aatatcgcttatttaagaactctgcttggttttcttggcaacaggga ctttacccaagaggtaatattccccctgctggaagtttggttttcgaa agatggcgtgatagacaaacaggtcaaaggttcttacgtctgtacttc caggctcaatcgttggatcaaatcagacagttgtcaccactttctaca ttatccccacctttaaaaaccgagttctctcgtcctggttgcaggcag ttgtcacttggcgttctctgtccctggactgagtccatgcaaagaatg agagctgctatcgacccaactgcgttgcctacagtgcagtacagacca taa One aspect of the present invention is to identify and provide suitable mutations in the *Serratia odorifera* wild type gene sequence in order to enhance and improve the expression of the protein in a host cell. The non-mutated or unmodified wild type nucleotide sequence has been described in WO 2011/141613 A2 (which is incorporated by reference) and is herein referred to as SEQ ID NO: 2 (see FIG. 6A):

SEQ ID NO: 2

```
atgttgctattgcaaaaggactggtcgcgtctgttatttgccgtcacg ctgggtatgatttccagcgtagcccaggctgagccgcgctacgtattg gaaaaggtggttgaggtcagccgccacggcgtacgcccgccgacctca ggcaaccggcaggcgatgcaggcgggaaccggccgagagtggccacaa tggctgacgcgcgacggcgaactcactggccacggttatgccgccgcc acgctgaaaggacgctatgaagccgactattatcgccgtcagggccta ttggccaacggctgtccgagcgcgggggcggtgtatgtctgggccagt ccgctacagcgcacgcgagccaccgcacaggcgttgatggacggcgca tttcccggctgcggggtcgccattcatgcggccgccaccgaacaggac cccctgtttcaggcagataaaatgggcctggtgccgctcgatgccgaa cgggctcgcacggcaataaggcaggcaatgggcggcagcgccgagcag gtgaaaacgcgctttagcgctgacattcggcgtctgcaagcggcggtc tgcctgccgcaacaggcttgcccggcctttgaacaaccgtgggaaatc actcaggagcacgacggccgcttcagcatcaacggtctggggacgttg tccaacatggcggaaagcattcgcctggcctacagcgaaaaccagccg acggcgcaggtcgcctttggccacggtgtcaacgcatcggccgtcgcg ccgttgctgcccctgctcaccgcccgctatgactttaccaatgacgtg ccctatatcgcgcaacgcggtggctcggtgctgttaaaccaaatcgcg ctggcgctggccgccgatcgaacctctgccggggcgccaccggcggcg
```

-continued

```
cgctggttgctgtttgtcgcgcatgacaccaatatcgcttatctgcgc accctgcttggctttagctggcaacaggggctttacccacgcggcaat attcccccggctggcagtctggtattcgaacgctggcgcgatcggcaa acgggccagcgcttcctgcgtctgtacttccaggcgcaatcgctggat caaatccgccagttgtcaccgctgagcacgctgtcgccaccgttaaaa accgagttcagccgtcctggctgccggcagttgtcactgggcgtactc tgtccctggactgagtcgatgcaacggatgcgcgcggctatcgacccg acggcgctgcctacggtgcagtaccggccataa
```

The optimized *Serratia odorifera* phytase nucleotide sequence according to SEQ ID NO: 1 differs from the wild type nucleotide sequence according to SEQ ID NO: 2 by the presence of 211 point mutations or modifications in the nucleotide sequence.

The optimized *Serratia odorifera* phytase nucleotide sequence according to SEQ ID NO: 1 does not comprise the nucleotide sequence encoding for a N-terminal peptide signal sequence of the wild type sequence according to SEQ ID NO: 4. The signal peptide sequence in the above indicated wild type phytase sequence according to SEQ ID NO: 2 is highlighted in grey.

The wild type coding sequence without the signal peptide sequence is herein referred to as SEQ ID NO: 8.

A sequence comparison of the sequence of SEQ ID NO: 1 with SEQ ID NO: 2 is depicted in FIG. 6 E. Each mismatch in the sequence alignment corresponds to a mutated or modified position, where the nucleotide with respect to the original sequence was changed to another nucleotide.

Referring to the sequence alignment according to FIG. 6E, the optimized *Serratia odorifera* phytase nucleotide sequence according to SEQ ID NO: 1 differs from the wild type nucleotide sequence according to SEQ ID NO: 8 by 211 point mutations or modifications in the nucleotide sequence.

Expression of the nucleotide sequence according to SEQ ID NO: 1 results in the polypeptide sequence of the *Serratia odorifera* phytase as shown in FIG. 6C (SEQ ID NO: 3). SEQ ID NO: 3, corresponds the polypeptide sequence of the mature phytase protein. As seen in the sequence alignment of FIG. 6C, the translated polypeptide sequence of SEQ ID NO: 1 and SEQ ID NO: 2 share 100% identity, i.e. none of the 211 mutations described in SEQ ID NO: 1 resulted in an exchange of one of the encoded amino acids.

Preferably, the term "modification" or "mutation" within the meaning of the present invention refers to alterations of the nucleotide position of the wild type sequence, which do not result in the exchange of the encoded amino acid but to the change of the codon of a given amino acid, thus, to codon-adjusting or codon-optimizing nucleotide exchange.

As will be appreciated, codon-optimization is generally based on the codon usage in a specific host organism, in which a given nucleic acid sequence is expressed, i.e. translated to the corresponding protein. The codon-optimization of the nucleic acid encoding the *Serratia odorifera* phytase protein described herein takes into account the relative codon frequencies, the optimized GC content and the mRNA instabilities.

Generally, "Percent identity" (in %) refers to a quantitative measurement of the similarity between two sequences (DNA, amino acid or otherwise). Closely related species are expected to have a higher percent identity for a given sequence than would more distantly related species, and thus percent identity to a degree reflects relatedness. Percent identity is calculated by multiplying the number of matches in the pair by 100 and dividing by the length of the aligned region, including gaps. Identity scoring only counts perfect matches, and does not consider the degree of similarity of amino acids to one another. For the calculation only internal gaps are included in the length, not gaps at the sequence ends.

Percent Identity=(Matches×100)/Length of aligned region (with gaps)

"Percent (%) nucleic acid sequence identity" with respect to the nucleic acid sequence according to SEQ ID NO: 1 encoding a protein with phytase activity identified herein is defined as the percentage of nucleotides in a candidate sequence that are identical with the nucleotides in the nucleic acid sequence according to SEQ ID NO: 1, after aligning the sequences and introducing gaps, if necessary, to achieve the maximum percent sequence identity. Alignment for purposes of determining percent nucleic acid sequence identity can be achieved in various ways that are within the skill in the art by using publicly available computer software such as BLAST, BLAST-2, ALIGN or Megalign (DNAS-TAR) software.

For example, the percent nucleic acid sequence identity may be determined using the sequence comparison program NCBI-BLAST2 (Altschul et al., Nucleic Acids Res. 25: 3389-3402 (1997). The NCBI-BLAST2 sequence comparison program can be downloaded from http://www.ncbi.nlm nih.gov or otherwise obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

Where the length of the given nucleic acid sequence, i.e. AppAs-r optima sequence is not equal to the length of a comparison nucleic acid sequence, the percent identity is calculated as follows:

1. AppAs-r Optima is Shorter than the Comparison DNA:
   AppAs-r optima NNNNNNNNNNNNNN (length =14 nt)
   Comparison DNA NNNNNNXXXXXXXXXX (length = 16 nt)
   (The lengths of the sequences are exemplary)
   % nucleic acid sequence identity=(the number of identically matching nucleotides between the two nucleic acid sequence as determined by e.g. NCBI-BLAST2)× 100 divided by (the total number of nucleotides of the AppAs-r optima nucleic acid sequence)=6×100 divided by 14=42.9%

2. AppAs-r Optima is Longer than the Comparison DNA:
   AppAs-r optima NNNNNNNNNNNNN (length=12 nt)
   Comparison DNA NNNNNNXXXYY (length=9 nt)
   (The lengths of the sequences are exemplary)
   % nucleic acid sequence identity=(the number of identically matching nucleotides between the two nucleic acid sequence as determined by e.g. NCBI-BLAST2)× 100 divided by (the total number of nucleotides of the AppAs-r optima nucleic acid sequence)=4×100 divided by 12=33.3%

Hence, the length of the reference sequence (AppAs-r optima nucleic acid sequence) determines the length of the aligned region. It will be appreciated that this principle is applicable also for the comparison of polypeptide sequences.

The expressions "protein with phytase activity" or "phytase" as used herein both refer to meso-inositol hexaphosphate phosphohydrolases, which catalyze the dissociation of the phosphate groups from the phytic acid (IP6) or the phytate. The result of this enzymatic reaction is a free phosphate group and an ester of the phosphate inositol (IP5-IP1). Generally, phytases can be classified in two groups: microbial or fungal phytases (E.C. 3.1.3.8) or 3-phytase, which start to hydrolyze the phosphorus group placed on the C1 or C3 inositol ring or phytases of plants (E.C. 3.1.3.26) or 6-phytase, which start to hydrolyze preferably the phosphate group located on the C6 of the inositol ring.

Accordingly "phytase activity" as used herein refers to enzymatic reaction of hydrolyzing the phosphate groups from the phytic acid (IP6) or phytate. In one embodiment the enzymatic phytase activity is the phytase activity as described for the *Serratia odorifera* protein according to SEQ ID NO: 2.

The present invention also contemplates measuring the phytase activity. For instance, phytase activity can be measured with the assays as described in WO 2011/141613 A2 or described herein in Example 3, in which the specific activity was assessed by measuring the free phosphate or phosphorous concentration that was release by the phytase enzyme using the molybdate-vanadate acid method.

This method is based on APHA Standard Method 4500-P C. In acids, ortho-phosphate ions react with ammonium molybdate and ammonium vanadate to form yellow ammonium phosphoric vanadomolybdate, which can be photometrically analyzed at 415 nm. The intensity of the yellow color is proportional to phosphate concentration. However, the present invention also envisages also other methods or assays for measuring or determining and phytase activity which are within the routine of the person skilled in the art. An alternative method is the Molybdenum blue method. In an acidic medium, ortho-phosphates bond with ammonium molybdate to form molybdenic phosphoric acid. With the aid of a reducing agent this forms phosphorus molybdenum blue compound. Photometrical measurement of dye intensity can be performed at 880 nm.

In a specific aspect, the invention provides a nucleic acid sequence that lacks the N-terminal signal sequence and/or the initiating methionine and is encoded by a nucleotide sequence that encodes such an amino acid sequence as hereinbefore described.

The N-terminal signal peptide sequence of the *Serratia odorifera* wild type gene is defined by the nucleotide sequence according to SEQ ID NO: 4 and by the amino acid sequence according to SEQ ID NO: 5.

SEQ ID NO: 4:
atgttgctattgcaaaaggactggtcgcgtctgttatttgccgtcacg
ctgggtatgatttccagcgtagcccaggct

SEQ ID NO: 5:
MLLLQKDWSRLLFAVTLGMISSVAQA

The inventors of the present invention observed that the expression of the full length *Serratia odorifera* wild type phytase gene as shown in FIG. 6A (SEQ ID NO: 2) including the 26 AA signal peptide leads to an unstable protein which after expression quickly disappeared. The inventors of the present invention therefore observed that omission of the 26 AA signal peptide resulted in an enhanced expression (see Example 1).

In a specific embodiment, the invention describes the optimized AppAs-r sequence for the expression in a suitable host cell expression system. The optimized sequence takes into account codon usage bias of the host cell organism. In a one embodiment, the most preferred or most frequent codons for each amino acid in the given nucleic acid sequence encoding the protein with phytase activity as described herein are used. Alternatively, it may be sufficient to provide a partially optimized sequence, i.e. where a part of the codons of the nucleic acid sequence are adapted to the most favored codon. In some embodiments, it is sufficient to optimize the codons of some specific amino acids in the AppAs-r sequence.

Preferred embodiments of the present invention relate to a nucleotide sequence, where at least 5%, 10%, 20%, 25%, 30%, 35%, 40%, 45%, 50% of the codons of the wild type AppAs-r nucleic acid sequence are modified to the codons most favored by the host cell organism. In further preferred embodiments, at least 51%, 52%, 53%, 54%, 55%, 56%, 57%, 58%, or 59% of the codons in the nucleic acid sequence are modified to the codons most favored by the host cell organism. In further preferred embodiments, at least 61%, 62%, 63%, 64%, 65%, 66%, 67%, 68%, or 69% of the codons of the wild type nucleic acid sequence are modified to the codons most favored by the host cell organism. In further preferred embodiments, at least 71%, 72%, 73%, 74%, 75%, 76%, 77%, 78%, or 79% of the codons of the wild type nucleic acid sequence are modified to the codons most favored by the host cell organism. In further preferred embodiments, at least 81%, 82%, 83%, 84%, 85%, 86%, 87%, 88%, or 89% of the codons in the nucleic acid sequence are modified to the codons most favored by the host cell organism. In further preferred embodiments, at least 91%, 92%, 93%, 94%, 95%, 96%, 97%, 98%, or 99% of the codons of the wild type nucleic acid sequence are modified to the codons most favored by the host cell organism.

In preferred embodiments, the isolated nucleic acid molecule nucleic acid molecule differs from the corresponding wild type phytase nucleotide coding sequence according to SEQ ID NO: 8 by the presence of codon-optimizing mutations.

"Codon optimizing mutations" according to the present invention refers to silent mutations to the coding sequence that do not result to a change of the amino acid sequence. The use of the novel phytase nucleotide sequences comprising codon optimizing mutations according to the present invention has the surprising technical advantage over prior art phytase sequences that an improved expression in a given host cell organism is possible without negatively affecting phytase activity by changing the amino acid sequence, thus, the structure or function of the resulting phytase protein is preserved.

Further preferred embodiments of the present invention relate to a nucleotide sequence, wherein at least 5%, 10%, 20%, 25%, 30%, 35%, 40%, 45%, 50% of the wild type phytase nucleotide coding sequence according to SEQ ID NO: 8 are modified to the codons most favored by the host cell organism. In further preferred embodiments, 51%, 52%, 53%, 54%, 55%, 56%, 57%, 58%, or 59% of the codons of the wild type phytase nucleotide coding sequence according to SEQ ID NO: 8 are modified to the codons most favored by the host cell organism. In further preferred embodiments, 61%, 62%, 63%, 64%, 65%, 66%, 67%, 68%, or 69% of the codons of the wild type phytase nucleotide coding sequence according to SEQ ID NO: 8 are modified to the codons most favored by the host cell organism. In further preferred embodiments, 71%, 72%, 73%, 74%, 75%, 76%, 77%, 78%, or 79% of the codons of the wild type phytase nucleotide coding sequence according to SEQ ID NO: 8 are modified to the codons most favored by the host cell organism. In further preferred embodiments, 81%, 82%, 83%, 84%, 85%, 86%, 87%, 88%, or 89% of the codons of the wild type phytase nucleotide coding sequence according to SEQ ID NO: 8 are modified to the codons most favored by the host cell organism. In further preferred embodiments, at least 91%, 92%, 93%, 94%, 95%, 96%, 97%, 98%, or 99% of the codons of the wild type phytase nucleotide coding sequence according to SEQ ID NO: 8 are modified to the codons most favored by the host cell organism.

In some embodiments, the isolated nucleic acid sequence comprises at least 1, 2, 3, 4, 5, 6, 7, 8, 9, or 10 codon optimizing mutations with respect to the host cell organism.

In yet further embodiments of the present invention; the isolated nucleic acid sequence comprises at least 10, 20, 30, 40, 50, 60, 70, 80, 90, or 100 codon optimizing mutations with respect to the host cell organism.

In further preferred embodiments of the present invention, the isolated nucleic acid sequence comprises at least 110, 120, 130, 140, 150, 160, 170, 180, 190, 200, or 210 codon optimizing mutations with respect to the host cell organism.

In most preferred embodiments all codons of the isolated nucleic acid sequence are codon-optimized with respect to the host cell organism.

In some embodiments 99, 98, 97, 96, 95, 94, 93, 92, 91 and 90% of all amino acid position use the most preferred codon of the host cell.

In further specific embodiments, the nucleic acid sequence has been optimized taking into account the codon usage bias in the methylotrophic yeast *Pichia pastoris*. In specific embodiments, as further described in Example 5 below, the original codons were analyzed one by one and changed to most preferred codon for each amino acid in *P. pastoris*. Codon usage bias in *P. pastoris* was previously described in Bai et al. (Bai J., Swartz D. J., Protasevich Brouillette C. G., Harrell P. M., Hidebrandt E., Gasser B., Mattanovich D., Ward A., Chang G. and Urbatsch I. L. (2011) A gene optimization strategy that enhances production of fully functional P-glycoprotein in *Pichia pastoris*. PLosOne 6:1-15), Sinclair et al. (Sinclair G. and Choy F. Y. M. (2002) Synonymous codon usage bias and the expression of human glucocerebrosidase in the methylotrophic yeast *Pichia pastoris*. Protein Expression and Purification 26:96-105) and Huang et al. (Huang H, Yang P, Luo H, Tang H, Shao N, et al. (2008) High-level expression of a truncated 1,3-1,4-beta-D-glucanase from *Fibrobacter succinogenes* in *Pichia pastoris* by optimization of codons and fermentation. Appl Microbiol Biotechnol. 78: 95-103.).

The term "expression construct" or "expression cassette" can be used interchangeably herein and refer to a nucleic acid sequence capable of directing expression of a particular nucleotide sequence in an appropriate host cell, comprising a promoter operably linked to the nucleotide sequence of interest which is operably linked to termination signals. It typically comprises sequences required for proper translation of the nucleotide sequence. The coding region usually codes for a protein of interest. The expression cassette comprising the nucleotide sequence of interest may be chimeric, meaning that at least one of its components is heterologous with respect to at least one of its other components. The expression cassette may also be one which is naturally occurring but has been obtained in a recombinant form useful for heterologous expression. Typically, however, the expression cassette is heterologous with respect to the host, i.e., the particular DNA sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter which initiates transcription only when the host cell is exposed to some particular external stimulus. In one embodiment, the expression vector includes a reporter gene operatively linked for expression with the nucleotide sequence encoding the polypeptide with phytase activity.

"Heterologous" as used herein means "of different natural origin" or represents a non-natural state. For example, if a host cell is transformed with a nucleic acid sequence derived from another organism, particularly from another species, that nucleic acid sequence is heterologous with respect to that host cell and also with respect to descendants of the host cell which carry that nucleic acid sequence. Similarly, heterologous refers to a nucleotide sequence derived from and inserted into the same natural, original cell type, but which is present in a non-natural state, e.g. a different copy number, or under the control of different regulatory elements.

"Regulatory elements" generally refer to sequences involved in conferring the expression of a nucleotide sequence. Regulatory elements comprise commonly a promoter operably linked to the nucleotide sequence of interest and termination signals. They also typically encompass sequences required for proper translation of the nucleotide sequence. "Regulatory elements" suitable for prokaryotes, for example, include a promoter, optionally an operator sequence, and a ribosome binding site. Eukaryotic cells are known to utilize promoters, polyadenylation signals, and enhancers.

The term "operably linked" as used herein means that a nucleic acid sequence is placed into a functional relationship with another nucleic acid sequence. For example, DNA for a presequence or secretory leader is operably linked to DNA for a polypeptide if it is expressed as a preprotein that participates in the secretion of the polypeptide; an promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. Enhancers are not necessarily contiguous. Linking is accomplished by ligation at convenient restriction sites. If such sites do not exist, the synthetic oligonucleotide adaptors or linkers are used in accordance with common practice.

Suitable "expression vectors" or "expression plasmids" for the expression of the optimized phytase gene according to the present invention in the various expression systems are well within the skill of the art. Suitable expression vectors for the expression in yeast *Pichias*, for instance, include, but is not limited thereto, the pPIC series of vectors. These vectors use the AOX1 promoter which is inducible with methanol. The expression plasmids may contain elements for insertion of foreign DNA into the yeast genome and signal sequence for the secretion of expressed protein.

The optimized phytase protein according to the present invention can be expressed in any suitable host cell protein expression system. Commonly used protein expression systems include those derived from bacteria, yeast, baculovirus/insect, and mammalian cells, and the filamentous fungi such as the commercially relevant fungus *Myceliophthora thermophile*. Suitable bacterial system include, but are not limited thereto, *Escherichia coli, Corynebacterium*, or *Pseudomonas fluorescens*. Eukaryotic expression systems include yeast systems such as *Saccharomyces cerevisiae, Pichia Pastoris*, or *Kluyveromyces lactis*. The present invention also contemplates the use of other fungal expression systems such as filamentous fungi like *Aspergillus, Trichoderma* and *Myceliophthora thermophila*, C1, recently described for the production of diverse industrial enzymes. Further Eukaryotic expression systems include Baculovirus-infected cell, for example, infected insect cells such as Sf9, Sf21, High Five strains or mammalian cells such as HeLa, and HEK 293, which also allows expression of glycosylated proteins that cannot be expressed using yeast or prokaryotic cells (like *E. coli*). It is very useful system for expression of proteins in high quantity. Further suitable eukaryotic expression systems also include non-lytic insect cell expression as an alternative to the lytic baculovirus expression system, the protozoan *Leishmania tarentolae* (non pathogenic strain) expression system, as well as plant systems (e.g. Tobacco) and Mammalian systems such as *Bos primigenius* (Bovine), *Mus musculus* (Mouse), Chinese Hamster Ovary, Human Embryonic Kidney cells, and Baby Hamster Kidney.

In yet a further preferred embodiment the fungal cell is *Pichia Pastoris* (see Cregg J M, Cereghino J L, Shi J, Higgins D R (September 2000). "Recombinant protein expression in *Pichia pastoris*". Mol. Biotechnol. 16 (1): 23-52). Suitable *Pichia pastoris* strains for the protein expression as describe herein include GS 115, X33, or KH71H (Invitrogen, 1600 Faraday Avenue, Carlsbad, Calif., 92008, USA). In a preferred embodiment the *Pichia pastoris* strain is KH71H.

For expression of the novel phytase nucleotide nucleic acid molecule of the present invention, the gene is cloned into a suitable expression vector comprising said nucleic acid molecule or the expression construct as described herein in the examples.

The present invention relates to a method of producing a protein having the enzymatic activity of a phytase comprising the steps of:
  a) introducing into a host cell a the expression vector comprising:
    i) elements regulating the expression that are functional in the host cell; and
    ii) operatively linked thereto a nucleic acid molecule as defined herein;
  b) cultivating the host cells obtained in step a) under conditions suitable for expression of the protein, and optionally
  c) recovering the protein produced in step b) from the cell culture.

The step of introducing the expression vector is commonly known as "transformation", which is defined as the genetic alteration of a cell resulting from the direct uptake and incorporation of exogenous genetic material (exogenous DNA) from its surroundings and taken up through the cell membrane(s). Methods for transforming a given host cell with the expression vector or expression construct as well as the optimal conditions generally depend on the host cell and are within the skill of the art. Accordingly, the skilled person is well aware of the specific conditions for inducing expression in the host cell and cultivating the host cell in an appropriate medium.

The terms "recovering" and "purifying" can be used herein interchangeably and refer to the separating out the expressed polypeptide from the culture to obtain a pure or substantially pure amount of the polypeptide, i.e. separated from other proteins and/or lipids and/or nucleic acids and/or components of the host cell in the culture. Within the meaning of the present invention said step of recovering comprises i) separating the secreted protein from the medium and/or i) separating the protein from the host cell.

In a specific embodiment, the optimized phytase protein of the present invention is expressed in the yeast *Pichia pastoris*. Recombinant protein production in the yeast *Pichia pastoris* has several advantages over other eukaryotic and prokaryotic expression systems, namely: rapid growth rate, high cell-density fermentation, productivity in an almost protein-free medium; elimination of endotoxin and bacteriophage contamination, diverse posttranslational modifications that include polypeptide folding, glycosylation, methylation, acylation, proteolytic adjustment, and targeting to subcellular compartments; and easy purification from growth medium.

Most *P. pastoris* expression systems are based on methanol-induced alcohol oxidase (AOX1) promoter (see Romanos, M. A., Scorer, C. A., & Clare, J. J. (1992). Yeast, 8, 423-488.) Upon induction by methanol, the fraction of total soluble protein that is composed of alcohol oxidase can typically rise to 30%. Commonly used *P. pastoris* expression vectors comprise the following elements: (1) 5'-AOX1 (the alcohol oxidase promoter upstream of the gene of interest); (2) SIG (a secretion signal sequence); (3) MCS (a multiple cloning site); (4) TT (a transcription termination site); (5) HIS4 (a marker for selection by hydroxyhistidinase); (6) Ampr (for selection with ampicillin); and (7) ColB1 (a replication element for plasmid propagation in *E. coli*) (see Li, P. Z., Gao, X.-G., Arellano, R. O., & Renugopalakrishnan, V. (2001). Protein Expression and Purification, 22, 369-380.)

Further suitable, commercially available vector systems for expression *P. pastoris* include the pPICZαA, B, and C vectors (*Pichia* Expression Kit K1710-01 or EasySelect™ *Pichia* Expression Kit no. K1740-01 pursued from Invitrogen), which are based on the selection of the recombinant protein with Zeocin®.

In a further aspect the present invention relates to protein obtained by the method according to the invention. The methodology described herein results in the producing of a codon-optimized *Serratia odorifera* phytase protein according to the polypeptide sequence of SEQ ID NO: 2. The expressed gene product of the designed and optimized *Serratia odorifera* gene corresponds to the mature protein lacking the first 26 amino acids, i.e. after cleavage of the signal peptide in the cell, which has a molecular weight of about 45 to 46 kD as can be seen in the SDS gel in FIG. 1, which shows that at the same expression conditions and at the same sample loading, the expression level of the AppAs-r optima gene is substantially higher than that of the AppAs-r gene.

Figures 7, 8:
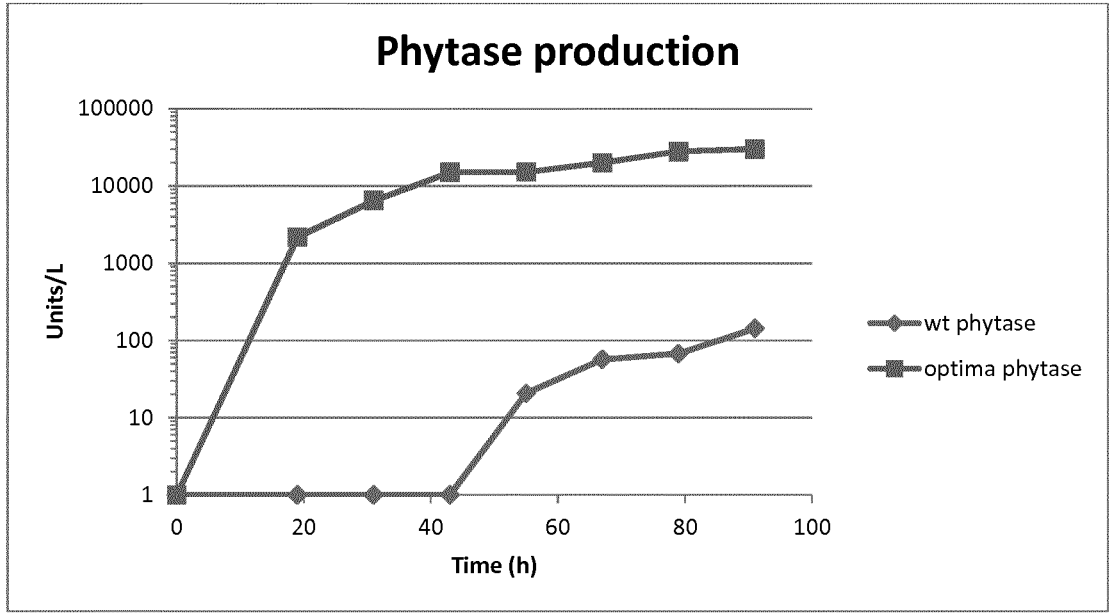
FIG. 7: Expression profiles of the wild type phytase and an improved phytase (optima phytase)
FIG. 8 Graph showing phytase production (Units/L) over time (h) of wild type phytase as compared to improved phytase (optima phytase)

As evidenced by Example 5, and FIGS. 7 and 8, it was surprisingly found the use of codon-optimized sequence SEQ ID NO: 1 resulted in an improved expression as compared to the expression of the corresponding wt type phytase sequence according to SEQ ID NO: 2 or SEQ ID NO: 8. In this context Example 5 demonstrates that expression of corresponding WT phytase sequence does not exceed 143 Units/L (U/L) while the Optima phytase can be expressed to an amount of up to 29973 Units/L. Example 5 demonstrates that the mutations made to the optima sequence, which takes into account the codon usage in the respective yeast host cell *Pichia Pastoris*, substantially contributed to an increased and effective protein expression, in which the amount of the expressed protein and the rate of expression is increased. Hence, the expression of the optimized *Serratia odorifera* phytase sequence resulted in a substantially improved protein expression.

In specific preferred embodiments, the expression of the isolated nucleic acid sequence is carried out in a *P. pastoris* expression system as described herein.

In yet further embodiments of the present invention, protein expression is carried out using methanol expression system as herein exemplary described in Example 1 or 5 and phytase activity was measured in U/L using the molybdate-vanadate method in acidic medium (ISO 300024:2009 (E)) as described in Example 3.

In preferred embodiments, the method according to the invention results in an improved expression, where the protein has a phytase activity of at least 250, 500, 750, or at least 1000 U/L as determined with the methods described herein.

In preferred embodiments, the method according to the invention results in an improved expression, where the protein has a phytase activity of at least 1500, 2000, 2500, 3000, 3500, 4000, 4500, 5000, 5500, 6000, 6500, 7000, 7500, 8000, 8500, 9000, 9500 or at least 10000 U/L as determined with the methods described herein. In yet further preferred embodiments, the method according to the invention results in an improved expression, where the protein has a phytase activity of at least 11000, 12000, 13000, 14000, 15000, 16000, 17000, 18000, 19000, or at least 20000 U/L as determined with the methods described herein.

Moreover, the optimized *Serratia odorifera* phytase sequence was analyzed with respect to phytase activity dependent on temperature, pH, the presence of proteases and the maintenance of phytase active over time in Example 3. Surprisingly, the results in Example 3 showed that the codon-optimized *Serratia odorifera* phytase protein obtained by the method according to the present invention resulted in a specifically stable protein with improved phytase activity.

The present invention further contemplates the use of the protein according to the present invention or produced by the method described herein for the manufacture of additives for animal feed.

The optimized phytase protein expressed by the methods as described herein has the following characteristics:
  a) Molecular weight of about 45 to 47 kDa, preferably about 46 kDa;
  b) pH optimum of between 2.0 an 9, preferably of between 2.5 and 8, even more preferably of between 3.0 and 7, and most preferably of from 3.3 and 5.8.
  c) enzymatic activity is of between 40 to 55° C., preferably at 50° C.;
  d) high specific activity at of more than 500 U/mg, preferably more than 600, 700, 800, 900, or 1000 U/mg, more preferably at about 1120+/−150 U/mg
  e) high resistance to proteases, preferably resistance to pepsin and trypsin
  f) Isoelectric point at 9.3.

In yet another aspect, the present invention relates to additives for animal feed comprising the protein described herein or comprising the protein produced by the method described herein. The additive can be adequately prepared on a solid or liquid basis. The additives may further comprise other enzymatic preparations commonly used for solid or liquid additive preparations, or commonly used in the preparation of animal feed. The additives for animal feed may comprise an effective amount of phytase sufficient for assimilation and enzymatic release of free phosphorous from phytate.

EXAMPLES

Example 1: Expression in *Pichia pastoris*

1. Construction of the Expression Vector.

To isolate the encoding area of the mature protein the following oligonucleotides were used:

```
SerrF:
                                    (SEQ ID NO: 6)
GCGCGCGAATTCGAGCCGCGCTACGTATTGG SerrR:
                                    (SEQ ID NO: 7)
GCGCGCAAGCTTGTCTAGACGTGGCCGGTACTGCACCG
```

The encoding area of the mature protein was amplified using the oligonucleotides SerrF and SerrR. The amplification product was visualized on an agarose gel, the band of the expected size was cut out and the DNA was extracted from the gel using the NucleoSpin Extract II Kit (Macherey-Nagel).

The purified DNA was inserted into the vector pPICZα A (Invitrogen, San Diego, Calif.) via the restriction sites of EcoRI and Xbal generated by the oligonucleotides. The EcoRI restriction site in SerrF and the Xbal restriction site in SerrR is highlighted in bold. The construction with the inserted purified DNA was transformed to DH5α cells, which were subsequently plated on LB medium containing 25 μg/ml Zeocin. The positive colonies were picked and the obtained vectors were subjected to sequencing. The positive clone with the correct sequence was cultivated in large amounts with the aim to obtain DNA for yeast transformation.

2. Transformation of Yeasts and Expression of the Protein

The strain of *Pichia pastoris* KH71H (Invitrogen) was cultivated on YPD medium and prepared for the transformation. 10 μg of plasmid pPICZα A AppAs-r was linearized by PmeI restriction enzyme and introduced into the yeast cells by shock with Lithium/Polyethylene.

The transformed yeast cells were plated on YPDZ medium containing 100 μg/ml Zeocin, which allowed the selection of colonies that have integrated the gene Sh ble (which product confers resistance to Zeocin) into the host chromosomal DNA. Only the transformants, which had integrated the gene Sh ble, will be able to grow on the YPDZ medium. After two days, the transformants were inoculated and cultivated on minimal medium containing glycerol (BMGY) for 24 hours, and subsequently the yeasts were collected by centrifugation (2.500 g, 3 min) and resuspended in a medium with 0.5% methanol (BMMY) for induction of the expression of the phytase gene.

3. Quantification of the Phytase Activity of the Transformants

A total of 61 transformants were analyzed and quantified with regard to phytase activity using the molybdate-vanadate method in acidic medium (ISO 300024:2009 (E)).

1.160 μl substrate solution (5 mM sodium phytate in 250 mM sodium acetate buffer, pH 5.5) was added to 40 μl diluted solution of the enzyme. The reaction was carried out at 37° C. for 30 minutes. Subsequently 800 μl STOP solution (14% nitric acid; 3.3% ammonium heptamolybdate tetrahydrate, 0.078% vanadate) was added to the solution to terminate the reaction. As a control, the STOP solution was added to the diluted solution of the enzyme for inactivation, which was then added the substrate solution. After 10 minutes, yellow color intensity was quantified at 415 nm and the activity of the enzyme solution and the respective control solution were quantified. One unit of phytase activity is defined as the amount of enzyme that liberates 1 μmol of phosphorus per one minute. Two days after methanol induction, 6 out of 61 transformants produced between 10 and 55 U/ml in cultivating medium. The obtained gene is a novel gene which encodes for a polypeptide with phytase activity. The polypeptide with phytase activity was termed AppAs-r.

Example 2: Purification of AppAs-r Polypeptide Expressed in *Pichia pastoris*

In order to purify the phytase produced in *Pichia pastoris*, the transformants with an activity of 55 U/ml were cultivated and induced at optimal conditions. Four days after the induction with methanol phytase activity was measured using the same method as in the previous examples resulting in activity of the supernatant of 163 U/L. The supernatant was obtained by centrifugation at 14.100 g during 5 minutes. The precipitated cells were discarded.

The supernatant was achieved through centrifugation with VIVASPIN 20 (50,000 MWCO (Sartorius Studium)). The concentrated solution was subsequently dialyzed in a sodium acetate buffer (0.25 M, pH 5.5). Finally the phytase was purified using gel filtration (Sephacryl S-200) with the same buffer as used for dialysis.

Example 3: Characterization of the AppAs-r Optima Expressed in *Pichia pastoris*

1. Determination of the Molecular Weight

The molecular weight of the phytase AppAs-r optima was characterized using a denaturing acrylamide gel (SDS-PAGE). FIG. 1 shows the result of the SDS-PAGE:
1) first lane corresponds to control (cultivation medium without methanol induction),
2) the second lane corresponds to expression in cultivation medium with methanol of phytase AppAs-r,
3) the third lane corresponds to expression in cultivation medium with methanol of phytase AppAs-r optima and
4) the fourth lane corresponds to the molecular weight marker.

The same volume of sample was loaded in lanes 1, 2 and 3.

As can be seen from FIG. 1, the AppAs-r optima molecular weight is about 46 KDa, which corresponds to the estimated molecular weight of the polypeptide sequence derived from the cloned DNA sequence. It can also be seen from the SDS-Gel that at the same expression conditions and at the same sample loading, the expression level of the AppAs-r optima gene is substantially higher than that of the AppAs-r gene.

Figure 2:
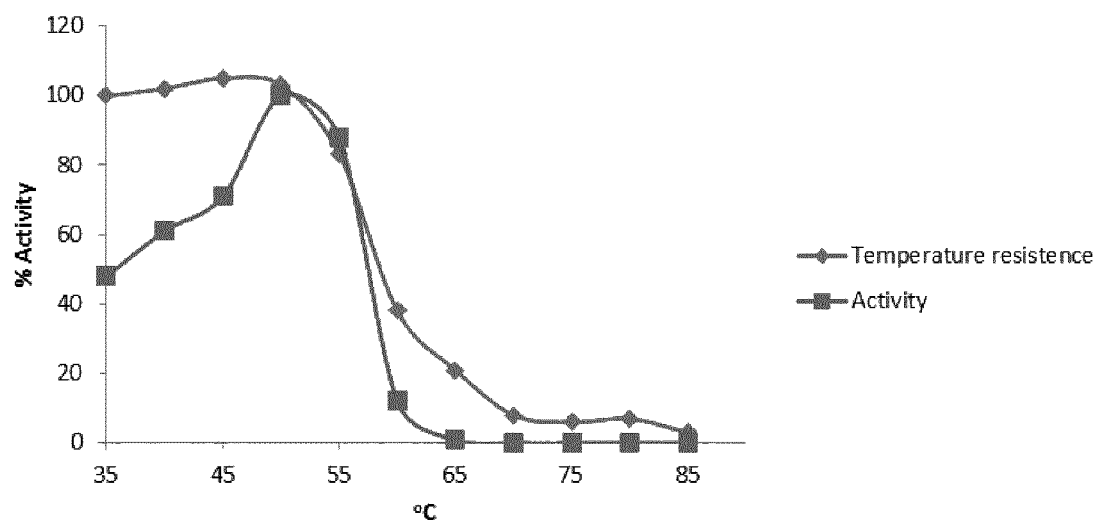
FIG. 2: Determination of the enzymatic activity (%) phytase AppAs-r optima protein dependent on the temperature (° C.) and the temperature resistance

2. Determination of the AppAs-r Optima Enzymatic Activity Depending in the Temperature As can be seen in FIG. 2, the enzyme activity changes with temperature. The optimal temperature was determined at 5.5 pH, which is the pH as required by ISO 300024:2009 (E). The activity was tested within the temperature range of between 35° C. and 85° C. The maximum activity was measured at 50° C. As shown in FIG. 2, after 10 minutes at 60° C. the enzyme still retains a 40% from its activity.

3. Determination of the AppAs-r Optima Enzymatic Activity Depending on the pH.

The effect of the pH on phytase activity was tested using the following buffers: Glycine-HCl for pH 1.5-3.5; sodium acetate for pH 3.5-6.0; Tris-HCl for pH 6.0-8.5; Glycine-NaOH for pH 8.5-10.0. All buffers contained 0.05% IGPAL.

Figure 3:
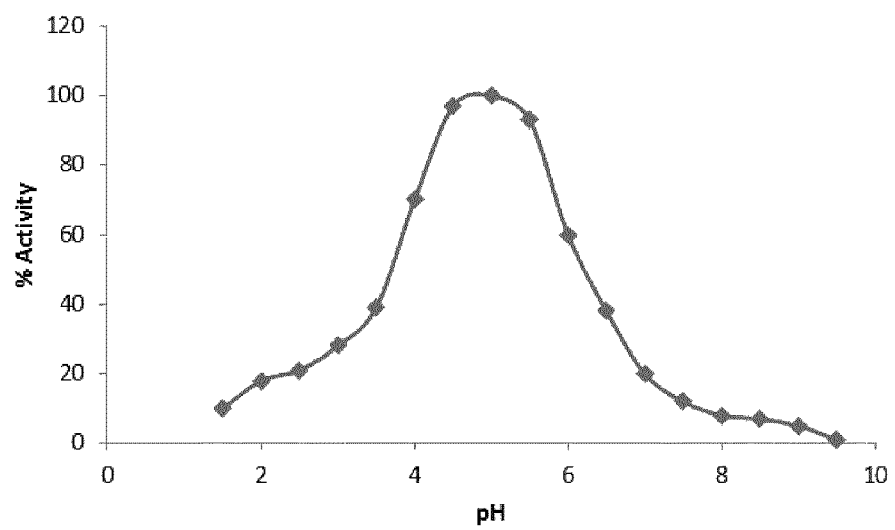
FIG. 3: Determination of the enzymatic activity of phytase AppAs-r optima protein depending on the pH

As can be seen in FIG. 3, the enzymatic activity changes with the pH. The maximum activity was observed at 5.0 pH. An activity of 70% is still maintained at 4.0 pH, while more than 80% activity is maintained at pH 5.5.

4. Effect of Proteases on the Enzymatic Activity

Figure 4:
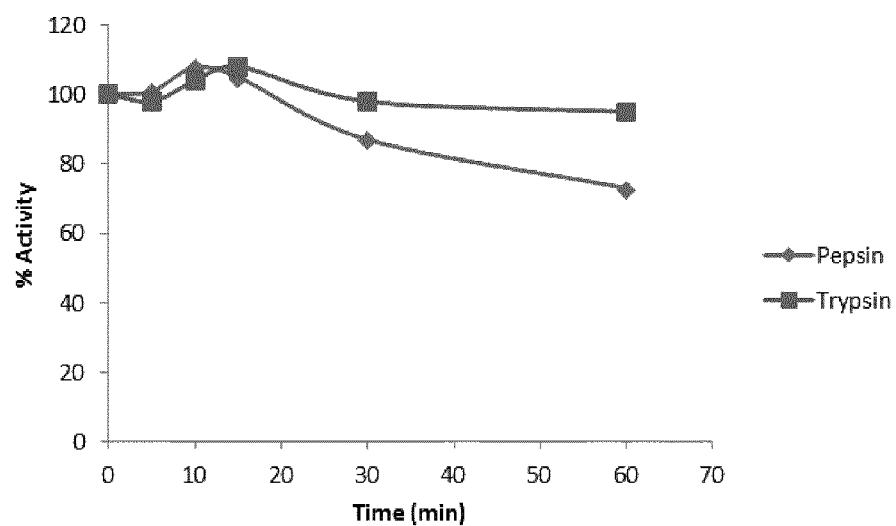
FIG. 4: Effect of the proteases pepsin (filled rhombus) and trypsin (filled square) on the enzymatic activity of AppAs-r optima.

In order to determinate the resistance to proteases, purified AppAs-r optima (1.6 mg/ml) was incubated with 5 mg/ml pepsin or 50 mg/ml trypsin at 37° C. After incubation at different incubation times (5; 10; 15; 30 and 60 minutes) the remaining phytase activity was quantified in the sample. As can be seen in FIG. 4, one hour after the incubation with pepsin the phytase AppAs-r retained more than the 70% (73%) of its initial activity and more than 90% (95%) of its initial activity one hour after incubation with trypsin. This indicates that the tested phytase is highly resistant to the activity of proteases, which can be very beneficial for use in animal feed.

5. Maintenance of the Phytase Activity Over Time

Figure 5:
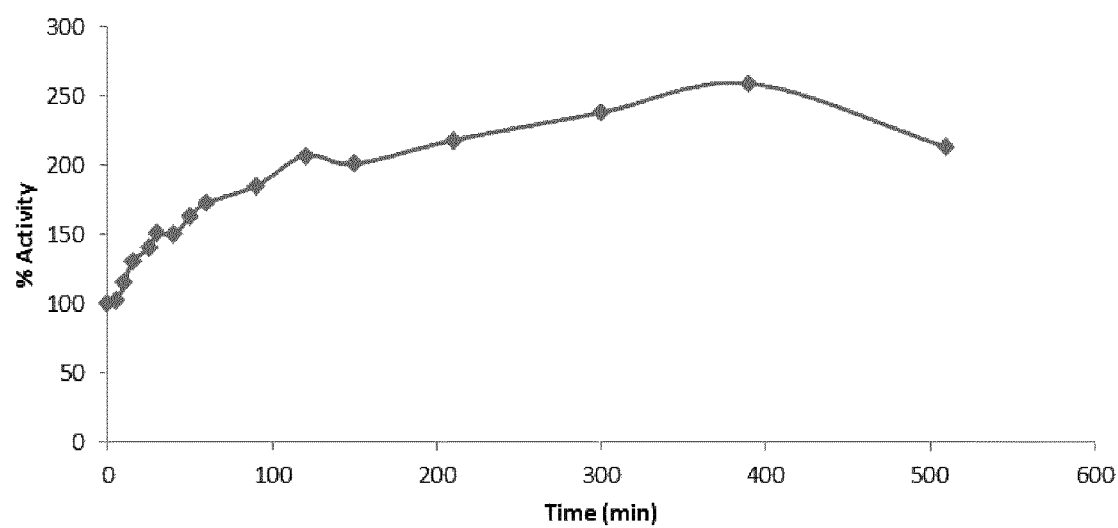
FIG. 5: Maintenance of AppAs-r optima phytase activity over time

To determinate the activity of the AppAs-r phytase over time, the specific activity per minute was determined at different time points after addition of the substrate. As can be derived from FIG. 5, AppAs-r differs from majority of the phytases in that it increases its specific activity over time. AppAs-r is still active within at least 8 hours after the substrate was added, and doubles its initial specific activity after 4½ hours of activity (FIG. 5). This increased and sustained activity over time has not been described for any other phytase. This is a very important issue because animal digestion usually takes more than 30 minutes and so that it is required that the enzyme remains active as long as possible. The increased and sustained activity over time can be also relevant with regard to liquid feed. Thus, this allows the release of the majority of the phosphorus present in form of phytate in the feed by using a lesser amount of enzyme.

6. Determination of the Specific Activity

In order to determine the specific activity, the concentration of the concentrated and purified AppAs-r phytase was measured using the Lowry method and the specific activity was assessed by molybdate-vanadate acid at 37° C. and pH 4.75. The resulting specific activity of purified AppAs-r was 1.123±112 U/mg.

Example 4: Release of Phosphate of Organic Material from the Soil

Due to the long activity of the phytase it was important to determine its ability to release inorganic phosphorus from organic material in the soil. The result of this assay was considered useful for the preparation of an additive for fertilizers. For this assay 5 soil samples were picked. 2.5 g of each sample was weighed and resuspended in an acetate buffer, and a final concentration of 0.25 g sample/ml was calculated and adjusted. The samples were incubated for 20 minutes under agitation at ambient temperature. After a ⅒ dilution of the samples with acetate buffer, the equivalent of 1 U of phytase AppAs-r/100 g soil was added to 1.2 ml of each sample and incubated for 24 hours at 25° C. The results show that the release of phosphorus was 53.6±27.8 mg of phosphorus/100 g soil, thus increased free phosphate of the soil by 23.4±18.1%.

Example 5: Comparative Expression of Wild Type Phytase Gene and a Modified Phytase Gene (Optima Phytase)

The inventors of the present invention observed that the expression of the full length *Serratia odorifera* wild type gene phytase gene as shown in FIG. 6A (SEQ ID NO: 2) including the 26 AA signal peptide leads to an unstable protein which after expression quickly disappeared. The inventors of the present invention therefore observed that omission of the 26 AA signal peptide (SEQ ID NO: 8) resulted in an enhanced expression (see Example 1).

Starting from this observation the vector pPICZα containing the nucleotide sequence encoding the mature *Serratia odorifera* wild type phytase as described in Example 1, it was further evaluated as to how the nucleotide sequence can be further modified in terms of an improved expression of the phytase protein in the host cell.

In order to obtain an improved AppAs-r sequence, the original codons were analyzed one by one and changed to most preferred codon for each amino acid in *P. pastoris*. Codon usage bias in *P. pastoris* was previously described in Bai et al. (Bai J., Swartz D. J., Protasevich Brouillette C. G., Harrell P. M., Hidebrandt E., Gasser B., Mattanovich D., Ward A., Chang G. and Urbatsch I. L. (2011) A gene optimization strategy that enhances production of fully functional P-glycoprotein in *Pichia pastoris*. PLosOne 6:1-15), Sinclair et al. (Sinclair G. and Choy F. Y. M. (2002) Synonymous codon usage bias and the expression of human glucocerebrosidase in the methylotrophic yeast *Pichia pastoris*. Protein Expression and Purification 26:96-105) and Huang et al. (Huang H, Yang P, Luo H, Tang H, Shao N, et al. (2008) High-level expression of a truncated 1,3-1,4-beta-D-glucanase from Fibrobacter *succinogenes* in *Pichia pastoris* by optimization of codons and fermentation. Appl Microbiol Biotechnol. 78: 95-103.).

In SEQ ID NO: 1, the most frequent codon usage in *P. pastoris* were analyzed, identified and applied. In SEQ ID NO: 1 all 211 codons of the wt coding sequence without the sequence encoding the the N-terminal signal peptide sequence have been optimized (SEQ ID NO: 8). The evaluation also takes into account that the frequency of the codon usage described in the literature, was to certain extent conserved in some *P. pastoris* genes encoding proteins with catalytic activity such as phosphatases and kinases.

The modified phytase polynucleotide comprising the optimized codon as shown by SEQ ID NO: 1 was obtained by gene synthesis. The modified phytase polynucleotide was purchased by GenScript Company (Spain) and inserted into the vector pPICZα A (Invitrogen, San Diego, Calif.) via the restriction sites of EcoRI and XbaI.

The resulting plasmid containing the AppAs-rOp gene was linearized by digestion with PmeI restriction enzyme and transformed into the yeast cells by shock with Lithium/Polyethylene as in Example 1.

The expressed gene product of the designed and optimized *Serratia odorifera* gene corresponds to the mature protein lacking the first 26 amino acids, i.e. after cleavage of the signal peptide in the cell, which has a molecular weight of about 45 to 46 kD as can be seen in the SDS gel in FIG. 1.

Starting from the vector pPICZα containing the nucleotide sequence encoding the mature *Serratia odorifera* wild type phytase as described in Example 1, the inventors of the present invention evaluated and tested point mutations in this nucleotide sequence which could lead to an improved expression of the phytase protein in the host cell. It was observed that the 211 point mutations as present in FIG. 6B (SEQ ID NO:1) as compared to the wild type phytase sequence (SEQ ID NO: 2) contributed to an effective and stable expression in the yeast *Pichia pastoris*. FIG. 6C shows a sequence alignment of the optima phytase sequence (SEQ ID NO:1) and the wild type phytase sequence (SEQ ID NO: 2). The mismatches indicate the point mutations made to the original gene sequence. The point mutations take the codons preferably used in the host cell yeast *Pichia pastoris*. As can be seen from FIG. 6D, which shows an alignment of the translated mature protein of SEQ ID NO:1 and SEQ ID NO:2, the 211 mutations are silent, i.e. none of the mutations lead to a different amino acid in the phytase polypeptide.

In order to determine whether the mutations made to SEQ ID NO: 1 indeed have an effect on yeast protein expression, the modified nucleotide sequence was expressed under the same conditions as in Example 1. In order to determine the expression profiles, samples were taken at time points 0, 19, 31, 43, 55, 67, 79 and 91 hours after methanol expression. The phytase activity was measured using the molybdate-vanadate method in acidic medium (ISO 300024:2009 (E)) as described in Example 3. AppAs-r of Example 3 was used as a comparative example.

The results are summarized in Table 1. The data of this comparative example are expressed logarithmically in the graph according to FIG. 7, which shows the activity expressed in Units/L versus time (h).

In FIG. 7, the expression profile of the wt phytase AppsAS-r (comparative example) is shown in blue (filled rhombus) and expression profile of the optima sequence is shown in red (filled squares). As can be seen from the graph, the wt phytase gene expression is not optimal. The first measurable products appear after 40 hours of induction. After 91 hours the saturation curve shows a maximal activity of 143 U/L. Surprisingly, the expression of the modified phytase gene sequence (optima sequence) shows a measurable phytase gene product immediately within the first hours of protein expression, which reaches saturation after about 20 to 30 hours of induction of gene expression. After 90 hours the phytase production was more than 200 fold. This increase in production was unexpected.

Example 5 thus demonstrates that the mutations made to the optima sequence, which takes into account the codon usage in the respective yeast host cell *Pichia Pastoris*, indeed contributed to an increased and effective protein expression.

TABLE 1

Expression profile of wild type phytase compared to optima phytase

| Wild type phytase (AppAs-r) Time after methanol induction (hours) | | | | | | | |
|---|---|---|---|---|---|---|---|
| 0 | 19 | 31 | 43 | 55 | 67 | 79 | 91 |

| | 0 | 19 | 31 | 43 | 55 | 67 | 79 | 91 |
|---|---|---|---|---|---|---|---|---|
| Units/ml | 0 | 0 | 0 | 0 | 0 | 0 | 0 | 0 |
| Units/L | 1 | 1 | 1 | 1 | 21 | 57 | 68 | 143 |

| Optima phytase (AppAs-r optima) Time after induction (hours) | | | | | | | |
|---|---|---|---|---|---|---|---|
| 0 | 19 | 31 | 43 | 55 | 67 | 79 | 91 |

| | 0 | 19 | 31 | 43 | 55 | 67 | 79 | 91 |
|---|---|---|---|---|---|---|---|---|
| Units/ml | 0 | 2 | 6 | 15 | 15 | 20 | 28 | 30 |
| Units/L | 1 | 2163 | 6430 | 14914 | 15059 | 19797 | 27846 | 29973 |

The invention claimed is:

1. An isolated nucleic acid molecule
   i) comprising the nucleotide sequence according to SEQ ID NO: 1 encoding a protein with phytase activity or
   ii) having a sequence identity of at least 83% to a nucleotide sequence according to SEQ ID NO: 1 encoding a protein with phytase activity.

2. The isolated nucleic acid molecule according to claim 1, wherein the nucleic acid molecule does not comprise a nucleotide sequence encoding for a N-terminal signal peptide.

3. The isolated nucleic acid molecule according to claim 1, further comprising codon-optimizing mutations with respect to a host cell organism.

4. The isolated nucleic acid molecule according to claim 3, wherein the host cell organism is *Pichias Pastoris*.

5. The isolated nucleic acid molecule according to claim 3, wherein the nucleic acid molecule differs from the corresponding wild type nucleotide coding sequence by the presence of at least 50 codon optimizing mutations.

6. The isolated nucleic acid molecule according to claim 3, wherein at least 50%, of the codons of the corresponding wild type nucleic acid sequence are modified to the codons most favored by the host cell organism.

7. The isolated nucleic acid molecule according to claim 3, wherein all codons in the isolated nucleic acid molecule are modified to the codons most favored by the host cell organism.

8. The isolated nucleic acid molecule according to claim 1, which encodes the amino acid sequence of the protein with phytase activity according to SEQ ID NO: 3.

9. An expression construct comprising the nucleic acid sequence of claim 1 operatively linked to elements regulating the expression of the nucleic acid sequence.

10. The expression construct according to claim 9, wherein the elements regulating the expression comprise a promoter functional in a host cell and optionally a termination sequence.

11. The expression construct according to claim 10, wherein the host cell is a fungal cell.

12. The expression construct according to claim 11, wherein the fungal cell is *Pichia pastoris*.

13. A vector comprising the nucleic acid molecule according to claim 1 or the expression construct according to claim 9.

14. A method of producing a protein having the enzymatic activity of a phytase comprising the steps of:
   a) introducing into a host cell a vector comprising:
      i) elements regulating the expression that are functional in the host cell; and
      ii) operatively linked thereto a nucleic acid molecule as defined in claim 1;
   b) cultivating the host cells obtained in step a) under conditions suitable for expression of the protein, and optionally
   c) recovering the protein produced in step b) from the cell culture.

15. The method according to claim 14, wherein the elements regulating the expression comprise a promoter functional in a host cell and optionally a termination sequence.

16. The method according to claim 14, wherein the host cell is yeast cell.

17. The method according to claim 16, wherein the yeast cell is *Pichia pastoris*.

18. The method according to claim 17, wherein the protein expression is carried out using a methanol expression system.

19. The method according to claim 14, wherein the protein recovered in step d) has a phytase activity of at least 1000 Units/L.

20. The method according to claim 14, wherein the step of recovering comprises a) separating the secreted protein from the medium and/or b) separating the protein from the host cell.

* * * * *

SEQUENCE LISTING

<160> NUMBER OF SEQ ID NOS: 8

<210> SEQ ID NO 1
<211> LENGTH: 1203
<212> TYPE: DNA
<213> ORGANISM: Serratia odorifera

<400> SEQUENCE: 1

```
gagcctagat acgttttgga aaaggtggtt gaggtctctc gacacggcgt tagaccacca        60
acctcaggta acagacaggc tatgcaagcg ggaaccggaa gggagtggcc acaatggctg       120
actcgtgacg gagaactaac tggacacggt tatgcagccg caacacttaa aggaagatac       180
gaagccgatt attatagacg tcagggccta ttggcaaacg gttgtccatc tgctgggggct      240 gtttacgtct gggctagtcc tctacaaaga acaagggcca ccgcacaggc tttgatggac       300
ggtgcatttc ccggatgcgg ggtcgccatt catgctgcag ccactgaaca agatcccttg       360
tttcaagcag ataagatggg tcttgttcca ctcgatgccg aaagggctag aactgcaata       420
aggcaggcaa tgggtggctc agccgagcaa gtgaagacac gttttagtgc tgacattagg       480
cgtctgcaag ctgctgtttg tttgcctcaa caggcttgtc ctgcctttga acaaccttgg       540
gaaattactc aagagcatga cggtagattc agcatcaatg gtctaggaac attgtccaat       600
atggctgaat ctattagact tgcctactct gaaaaccagc caacggctca agtcgcattt       660
ggacacggtg tcaacgcatc cgccgtcgct cctttgttac cactgctaac cgccagatat       720
gactttacca atgatgtgcc ctatatcgct caagagggtg gctccgttct gttaaaccaa       780
attgctttgg ctcttgccgc agataggact tctgccgggg cgccacctgc tgctcgttgg       840
ttgttatttg tcgctcatga caccaatatc gcttatttaa gaactctgct tggttttttct      900 tggcaacagg gactttaccc aagaggtaat attcccctg ctggaagttt ggttttcgaa        960
```

```
agatggcgtg atagacaaac aggtcaaagg ttcttacgtc tgtacttcca ggctcaatcg    1020
ttggatcaaa tcagacagtt gtcaccactt tctacattat ccccaccttt aaaaaccgag    1080
ttctctcgtc ctggttgcag gcagttgtca cttggcgttc tctgtccctg gactgagtcc    1140
atgcaaagaa tgagagctgc tatcgaccca actgcgttgc ctacagtgca gtacagacca    1200
taa                                                                  1203

<210> SEQ ID NO 2
<211> LENGTH: 1281
<212> TYPE: DNA
<213> ORGANISM: Serratia odorifera

<400> SEQUENCE: 2
atgttgctat tgcaaaagga ctggtcgcgt ctgttatttg ccgtcacgct gggtatgatt      60
tccagcgtag cccaggctga gccgcgctac gtattggaaa aggtggttga ggtcagccgc     120
cacggcgtac gcccgccgac ctcaggcaac cggcaggcga tgcaggcggg aaccggccga     180
gagtggccac aatggctgac gcgcgacggc gaactcactg ccacggtta  tgccgccgcc    240 acgctgaaag acgctatga  agccgactat tatcgccgtc agggcctatt ggccaacggc    300
tgtccgagcg cggggcggt  gtatgtctgg gccagtccgc tacagcgcac gcgagccacc    360
gcacaggcgt tgatggacgg cgcatttccc ggctgcgggg tcgccattca tgcggccgcc    420
accgaacagg accccctgtt tcaggcagat aaaatgggcc tggtgccgct cgatgccgaa    480
cgggctcgca cggcaataag gcaggcaatg ggcggcagcg ccgagcaggt gaaaacgcgc    540
tttagcgctg acattcggcg tctgcaagcg gcggtctgcc tgccgcaaca ggcttgcccg    600
gcctttgaac aaccgtggga aatcactcag gagcacgacg gccgcttcag catcaacggt    660
ctggggacgt tgtccaacat ggcggaaagc attcgcctgg cctacagcga aaaccagccg    720
acggcgcagg tcgcctttgg ccacggtgtc aacgcatcgg ccgtcgcgcc gttgctgccc    780
ctgctcaccg cccgctatga ctttaccaat gacgtgccct atatcgcgca acgcggtggc    840
tcggtgctgt taaaccaaat cgcgctggcg ctggccgccg atcgaacctc tgccggggcg    900
ccaccggcgg cgcgctggtt gctgtttgtc gcgcatgaca ccaatatcgc ttatctgcgc    960
accctgcttg gctttagctg gcaacagggg ctttacccac gcggcaatat tccccggct   1020 ggcagtctgg tattcgaacg ctggcgcgat cggcaaacgg gccagcgctt cctgcgtctg   1080
tacttccagg cgcaatcgct ggatcaaatc cgccagttgt caccgctgag cacgctgtcg   1140
ccaccgttaa aaaccgagtt cagccgtcct ggctgccggc agttgtcact gggcgtactc   1200
tgtccctgga ctgagtcgat gcaacggatg cgcgcggcta tcgacccgac ggcgctgcct   1260
acggtgcagt accggccata a                                             1281

<210> SEQ ID NO 3
<211> LENGTH: 400
<212> TYPE: PRT
<213> ORGANISM: Serratia odorifera

<400> SEQUENCE: 3

Glu Pro Arg Tyr Val Leu Glu Lys Val Val Glu Val Ser Arg His Gly
 1               5                  10                  15

Val Arg Pro Pro Thr Ser Gly Asn Arg Gln Ala Met Gln Ala Gly Thr
             20                  25                  30

Gly Arg Glu Trp Pro Gln Trp Leu Thr Arg Asp Gly Glu Leu Thr Gly
         35                  40                  45
```

His Gly Tyr Ala Ala Ala Thr Leu Lys Gly Arg Tyr Glu Ala Asp Tyr
 50                  55                  60

Tyr Arg Arg Gln Gly Leu Leu Ala Asn Gly Cys Pro Ser Ala Gly Ala
 65                  70                  75                  80

Val Tyr Val Trp Ala Ser Pro Leu Gln Arg Thr Arg Ala Thr Ala Gln
                 85                  90                  95

Ala Leu Met Asp Gly Ala Phe Pro Gly Cys Gly Val Ala Ile His Ala
            100                 105                 110

Ala Ala Thr Glu Gln Asp Pro Leu Phe Gln Ala Asp Lys Met Gly Leu
        115                 120                 125

Val Pro Leu Asp Ala Glu Arg Ala Arg Thr Ala Ile Arg Gln Ala Met
130                 135                 140

Gly Gly Ser Ala Glu Gln Val Lys Thr Arg Phe Ser Ala Asp Ile Arg
145                 150                 155                 160

Arg Leu Gln Ala Ala Val Cys Leu Pro Gln Gln Ala Cys Pro Ala Phe
                165                 170                 175

Glu Gln Pro Trp Glu Ile Thr Gln Glu His Asp Gly Arg Phe Ser Ile
            180                 185                 190

Asn Gly Leu Gly Thr Leu Ser Asn Met Ala Glu Ser Ile Arg Leu Ala
        195                 200                 205

Tyr Ser Glu Asn Gln Pro Thr Ala Gln Val Ala Phe Gly His Gly Val
210                 215                 220

Asn Ala Ser Ala Val Ala Pro Leu Leu Pro Leu Leu Thr Ala Arg Tyr
225                 230                 235                 240

Asp Phe Thr Asn Asp Val Pro Tyr Ile Ala Gln Arg Gly Gly Ser Val
                245                 250                 255

Leu Leu Asn Gln Ile Ala Leu Ala Leu Ala Ala Asp Arg Thr Ser Ala
            260                 265                 270

Gly Ala Pro Pro Ala Ala Arg Trp Leu Leu Phe Val Ala His Asp Thr
        275                 280                 285

Asn Ile Ala Tyr Leu Arg Thr Leu Leu Gly Phe Ser Trp Gln Gln Gly
290                 295                 300

Leu Tyr Pro Arg Gly Asn Ile Pro Pro Ala Gly Ser Leu Val Phe Glu
305                 310                 315                 320

Arg Trp Arg Asp Arg Gln Thr Gly Gln Arg Phe Leu Arg Leu Tyr Phe
                325                 330                 335

Gln Ala Gln Ser Leu Asp Gln Ile Arg Gln Leu Ser Pro Leu Ser Thr
            340                 345                 350

Leu Ser Pro Pro Leu Lys Thr Glu Phe Ser Arg Pro Gly Cys Arg Gln
        355                 360                 365

Leu Ser Leu Gly Val Leu Cys Pro Trp Thr Glu Ser Met Gln Arg Met
370                 375                 380

Arg Ala Ala Ile Asp Pro Thr Ala Leu Pro Thr Val Gln Tyr Arg Pro
385                 390                 395                 400

<210> SEQ ID NO 4
<211> LENGTH: 78
<212> TYPE: DNA
<213> ORGANISM: Serratia odorifera

<400> SEQUENCE: 4
atgttgctat tgcaaaagga ctggtcgcgt ctgttatttg ccgtcacgct gggtatgatt    60
tccagcgtag cccaggct                                                  78

<210> SEQ ID NO 5
<211> LENGTH: 26
<212> TYPE: PRT
<213> ORGANISM: Serratia odorifera

<400> SEQUENCE: 5

Met Leu Leu Leu Gln Lys Asp Trp Ser Arg Leu Leu Phe Ala Val Thr
1               5                   10                  15

Leu Gly Met Ile Ser Ser Val Ala Gln Ala
            20                  25

<210> SEQ ID NO 6
<211> LENGTH: 31
<212> TYPE: DNA
<213> ORGANISM: Serratia odorifera

<400> SEQUENCE: 6
gcgcgcgaat tcgagccgcg ctacgtattg g                                  31

<210> SEQ ID NO 7
<211> LENGTH: 38
<212> TYPE: DNA
<213> ORGANISM: Serratia odorifera

<400> SEQUENCE: 7
gcgcgcaagc ttgtctagac gtggccggta ctgcaccg                           38

<210> SEQ ID NO 8
<211> LENGTH: 1203
<212> TYPE: DNA
<213> ORGANISM: Serratia odorifera

<400> SEQUENCE: 8
gagccgcgct acgtattgga aaggtggtt gaggtcagcc gccacggcgt acgcccgccg      60
acctcaggca accggcaggc gatgcaggcg ggaaccggcc gagagtggcc acaatggctg    120
acgcgcgacg gcgaactcac tggccacggt tatgccgccg ccacgctgaa aggacgctat    180
gaagccgact attatcgccg tcagggccta ttggccaacg gctgtccgag cgcggggcg     240
gtgtatgtct gggccagtcc gctacagcgc acgcgagcca ccgcacaggc gttgatggac    300
ggcgcatttc ccggctgcgg ggtcgccatt catgcggccg ccaccgaaca ggaccccctg    360
tttcaggcag ataaaatggg cctggtgccg ctcgatgccg aacgggctcg cacggcaata    420
aggcaggcaa tggcggcag cgccgagcag gtgaaaacgc gctttagcgc tgacattcgg    480
cgtctgcaag cggcggtctg cctgccgcaa caggcttgcc cggcctttga caaccgtgg    540
gaaatcactc aggagcacga cggccgcttc agcatcaacg gtctggggac gttgtccaac    600
atggcggaaa gcattcgcct ggcctacagc gaaaaccagc cgacggcgca ggtcgccttt    660
ggccacggtg tcaacgcatc ggccgtcgcg ccgttgctgc cctgctcac cgcccgctat    720
gactttacca atgacgtgcc ctatatcgcg caacgcggtg gctcggtgct gttaaaccaa    780
atcgcgctgg cgctggccgc cgatcgaacc tctgccgggg cgccaccggc ggcgcgctgg    840
ttgctgtttg tcgcgcatga caccaatatc gcttatctgc gcaccctgct ggctttagc    900
tggcaacagg ggctttaccc acgcggcaat attccccgg ctggcagtct ggtattcgaa    960
cgctggcgcg atcggcaaac gggccagcgc ttcctgcgtc tgtacttcca ggcgcaatcg   1020
ctggatcaaa tccgccagtt gtcaccgctg agcacgctgt cgccaccgtt aaaaaccgag   1080
ttcagccgtc ctggctgccg gcagttgtca ctgggcgtac tctgtccctg gactgagtcg   1140

```
atgcaacgga tgcgcgcggc tatcgacccg acggcgctgc ctacggtgca gtaccggcca    1200
taa                                                                   1203
```